United States Patent
Melief et al.

(10) Patent No.: US 12,296,009 B2
(45) Date of Patent: May 13, 2025

(54) IMMUNOGENIC COMPOSITION FOR THE TREATMENT OF CANCER

(71) Applicants: Jeroen Melief, Sollentuna (SE); Rolf Valter Rikard Kiessling, Stockholm (SE)

(72) Inventors: Jeroen Melief, Sollentuna (SE); Rolf Valter Rikard Kiessling, Stockholm (SE)

(73) Assignee: APGEN THERAPUETICS AB, Sollentuna (SE)

( * ) Notice: Subject to any disclaimer, the term of this patent is extended or adjusted under 35 U.S.C. 154(b) by 874 days.

(21) Appl. No.: 16/647,711

(22) PCT Filed: Sep. 28, 2018

(86) PCT No.: PCT/EP2018/076539
§ 371 (c)(1),
(2) Date: Mar. 16, 2020

(87) PCT Pub. No.: WO2019/063829
PCT Pub. Date: Apr. 4, 2019

(65) Prior Publication Data
US 2020/0276287 A1    Sep. 3, 2020

(30) Foreign Application Priority Data

Sep. 29, 2017   (EP) .................................. 17194223

(51) Int. Cl.
| A61K 39/00 | (2006.01) |
| A61K 9/00 | (2006.01) |
| A61K 45/00 | (2006.01) |
| C07K 14/47 | (2006.01) |

(52) U.S. Cl.
CPC ...... *A61K 39/4622* (2023.05); *A61K 39/4611* (2023.05); *A61K 39/4615* (2023.05); *A61K 39/46449* (2023.05); *A61K 39/464491* (2023.05); *A61K 39/464499* (2023.05); *A61K 9/0019* (2013.01); *A61K 2039/55522* (2013.01); *A61K 45/00* (2013.01); *A61K 2239/31* (2023.05); *C07K 14/4703* (2013.01)

(58) Field of Classification Search
CPC .............. A61K 39/0011; A61K 9/0019; A61K 39/001102; A61K 39/00119; A61K 45/00; A61K 2039/5152; A61K 2039/55522; C07K 14/4703
See application file for complete search history.

(56) References Cited

U.S. PATENT DOCUMENTS

2002/0018767 A1   2/2002   Lee et al.

FOREIGN PATENT DOCUMENTS

| WO | 2004/050708 A2 | 6/2004 | |
| WO | WO-2016090219 A1 * | 6/2016 | ........... A61K 31/407 |

OTHER PUBLICATIONS

Wang, et al., Blood 2015 23:822 (Year: 2015).*
Da Motta, et al., Oncogene 2017 36:122 (Year: 2017).*
Wuefel, et al., Scientific Reports 2020 10:15750 (Year: 2020).*
Miller, et al., Ann N Y Acad Sci 2009 1182:69 (Year: 2009).*
Avendano, et al., Medicinal Chemistry of Anticancer Drugs (Second Edition) © 2015 by Elsvier B.V. (Year: 2015).*
Wen et al., Int. J Oncol. 2019 55:879 (Year: 2019).*
Li, et al., Cell Death and Disease 2018 9:761 (Year: 2018).*
Chen, et al., Invest Opthamol Vis Sci 2024 65(8):11 (Year: 2024).*
Attwell, et al., "Abstract 263: The investigational drug ZEN-3694, a novel BET-bromodomain inhibitor, inhibits multiple tumor immune escape mechanisms and has the potential to combine with immunoptherapies" Eur. J. Cancer (2016) 69:S88.
Attwell, et al., "The investigational drug ZEN-3694, a novel BET-bromodomain inhibitor, inhibits multiple tumor immune escape mechanisms and has the potential to combine with immunoptherapies" Poster P089 at 28th EORTC—NCI—AACR Symposium on Molecular Targets and Cancer Therapeutics (2016).
Wang, H., et al., "JQ1, a Selective Bromodomain Inhibitor, Augment the Immunogenicity of Mantle Cell Lymphoma by Influencing the Expression of PD-L1" Blood (2015) 126(23):822.
Shimamura, T., et al., "Efficacy of BET Bromodomain Inhibition in Kras-Mutant Non-Small Cell Lung Cancer" Clinical Cancer Research (2013) 19(22):6183-6192.
Kagoya, Y., et al., "BET bromodomain inhibition enhances T cell persistence and function in adoptive immunotherapy models" J. Clin. Invest. (2016) 126(9):3479-3494.
Wolchok, J.D., et al., "Nivolumab plus Ipilimumab in Advanced Melanoma" N. Engl. J. Med. (2013) 369:122-33.
Kenter, G.G., et al., "Vaccination against HPV-16 Oncoproteins for Vulvar Intraepithelial Neoplasia" N. Engl. J. Med. (2009) 361:1838-47.
Aranda, F., et al., "Adoptive cell transfer for anticancer immunotherapy" Onco Immunology (2014) 3:e28344.
Poschke, I., et al., "A phase I clinical trial combining dendritic cell vaccination with adoptive T cell transfer in patients with stage IV melanoma" Cancer Immunol. Immunother. (2014) 63:1061-1071.
Schreibelt, G., et al., "Effective Clinical Responses in Metastatic Melanoma Patients after Vaccination with Primary Myeloid Dendritic Cells" Clin. Cancer Res. (2015) 22(9):2155-66.

(Continued)

*Primary Examiner* — Julie Wu
*Assistant Examiner* — Sydney Van Druff
(74) *Attorney, Agent, or Firm* — Robert C. Netter, Jr.; Dann, Dorfman, Herrell & Skillman

(57) ABSTRACT

The invention relates to the field of immunotherapy, more in particular to a composition for use in the treatment of cancer. The invention also relates to a composition obtainable by such a method, such as a pharmaceutical composition. More in particular, the invention relates to an ex vivo method for obtaining a composition suitable for the treatment of cancer in a subject, comprising the steps of providing primary tumor cells derived from the subject, and ex vivo contacting the tumor cells with an inhibitor of a bromodomain and extra-terminal domain family member (BET inhibitor).

5 Claims, 25 Drawing Sheets

(56) References Cited

OTHER PUBLICATIONS

Sahin, U., et al., "Personalized RNA mutanome vaccines mobilize poly-specific therapeutic immunity against cancer" Nature (2017) 547:222-226.
Ott, P.A., et al., "An Immunogenic Personal Neoantigen Vaccine for Melanoma Patients" Nature (2017) 547(7662): 217-221.
Zaretsky, J.M., et al., "Mutations Associated with Acquired Resistance to PD-1 Blockade in Melanoma" N. Engl. J. Med. (2016) 375(9): 819-829.
Zhu, H., et al., "BET Bromodomain Inhibition Promotes Anti-tumor Immunity by Suppressing PD-L1 Expression" Cell Reports (2016) 16:2829-2837.
Hogg, S.J., et al., "BET-Bromodomain Inhibitors Engage the Host Immune System and Regulate Expression of the Immune Checkpoint Ligand PD-L1" Cell Reports (2017) 18:2162-2174.
Filippakopoulos, P., et al., "Targeting bromodomains: epigenetic readers of lysine acetylation" Nature Reviews Drug Discovery (2014) 13:337-356.
Filippakopoulos, P., et al., "Selective inhibition of BET bromodomains" Nature (2010) 468:1067-1073.
Zuber, J., et al., "RNAi screen identifies Brd4 as a therapeutic target in acute myeloid leukaemia" Nature (2011) 478 (7370):524-528.
Puissant, A., et al., "Targeting MYCN in Neuroblastoma by BET Bromodomain Inhibition" Cancer Discov. (2013) 3 (3):308-323.
Segura, M.F., et al., "BRD4 Sustains Melanoma Proliferation and Represents a New Target for Epigenetic Therapy" Cancer Res. (2013) 73(20):6264-76.
Delmore, J.E., et al., "BET bromodomain inhibition as a therapeutic strategy to target c-Myc" Cell (2011) 146(6): 904-917.
Mertz, J.A., et al., "Targeting MYC dependence in cancer by inhibiting BET bromodomains" PNAS (2011) 108 (40):16669-16674.
Gowrishankar, K., et al., "Inducible but Not Constitutive Expression of PD-L1 in Human Melanoma Cells Is Dependent on Activation of NF-κb" PLoS One (2015) 10(4):e0123410.
Casey, S.C., et al., "MYC regulates the antitumor immune response through CD47 and PD-L1" Science (2016) 352:227-331.
Selvan, S.R., et al., "Establishment of stable cell lines for personalized melanoma cell vaccine" Melanoma Research (2010) 20:280-292.
Spranger, S., et al., "Up-Regulation of PD-L1, Ido, and Tregs in the Melanoma Tumor Microenvironment Is Driven by CD8+ T Cells" Science Translational Medicine (2013) 5(200):200ra116.
Patel, S.J., et al., "Identification of essential genes for cancer immunotherapy" Nature (2017) 548(7669):537-542.
Allard, D., et al., "Targeting the CD73-adenosine axis in immuno-oncology" Immunology Letters (2019) 205:31-39.
Cavallo, F., et al., "2011: the immune hallmarks of cancer" Cancer Immunol. Immunother. (2011) 60:319-326.
Dijkstra, K.K., et al., "Generation of tumor-reactive T cells by co-culture of peripheral blood lymphocytes and tumor organoids" Cell (2018) 174(6): 1586-1598.
Donia, M., et al., "Aberrant Expression of MHC Class II in Melanoma Attracts Inflammatory Tumor-Specific CD4p TCells, Which Dampen CD8p T-cell Antitumor Reactivity" Cancer Res. (2015) 75(18):3747-59.
Fransen, M.F., et al., "Local Activation of CD8 T Cells and Systemic Tumor Eradication without Toxicity via Slow Release and Local Delivery of Agonistic CD40 Antibody" Clin. Cancer Res. (2011) 17(8):2270-80.
Fransen, M.F., et al., "Controlled Local Delivery of CTLA-4 Blocking Antibody Induces CD8p T-Cell-Dependent Tumor Eradication and Decreases Risk of Toxic Side Effects" Clin. Cancer Res. (2013) 19(19):5381-9.
Hemon, P., et al., MHC Class II Engagement by Its Ligand LAG-3 (CD223) Contributes to Melanoma Resistance to Apoptosis Journal of Immunology (2011) 186:5173-5183.
Holmgaard, R.B., et al., "Tumor-Expressed IDO Recruits and Activates MDSCs in a Treg-Dependent Manner" Cell Reports (2015) 13:412-424.
Hornyak, L., et al., "The Role of indoleamine-2,3-Dioxygenase in Cancer Development, Diagnostics, and Therapy" Frontiers in Immunology (2018) 9:151.
Ishihara, J., et al., "Matrix-binding checkpoint immunotherapies enhance antitumor efficacy and reduce adverse events" Sci. Transl. Med. (2017) 9:eaan0401.
Khan, A.N.H., et al., "Histone deacetylase inhibitors induce TAP, LMP, Tapasin genes and MHC class I antigen presentation by melanoma cells" Cancer Immunol. Immunother. (2008) 57(5): 647-654.
Kim, Y.H., et al., "In situ vaccination against mycosis fungoides by intratumoral injection of a TLR9 agonist combined with radiation: a phase 1/2 study" Blood (2012) 119(2):355-363.
Landsberg, J., et al., "Melanomas resist T-cell therapy through inflammation-induced reversible dedifferentiation" Nature (2012) 490:412-416.
Marabelle, A., et al., "Intratumoral immunotherapy: using the tumor as the remedy" Annals of Oncology (2017) 28 (Supplement 12): xii33-xii43.
McGranahan, N., et al., "Allele-Specific HLA Loss and Immune Escape in Lung Cancer Evolution" Cell (2017) 171: 1259-1271.
Munn, D.H., et al., "Indoleamine 2,3 dioxygenase and metabolic control of immune responses" Trends Immunol. (2013) 34(3):137-143.
Respa, A., et al., "Association of IFN-g Signal Transduction Defects with Impaired HLA Class I Antigen Processing in Melanoma Cell Lines" Clin. Cancer Res. (2011) 17(9):2668-2678.
Sagiv-Barfi, I., et al., "Eradication of spontaneous malignancy by local immunotherapy" Sci. Transl. Med. (2018) 10: eaan4488.
Setiadi, A.F., et al., "Epigenetic Enhancement of Antigen Processing and Presentation Promotes Immune Recognition of Tumors" Cancer Res. (2008) 68(23):9601-9607.
Woo, S.R., et al., "Immune Inhibitory Molecules LAG-3 and PD-1 Synergistically Regulate T-cell Function to Promote Tumoral Immune Escape" Cancer Res. (2012) 72(4):917-27.
Van Der Burg, S.H., et al., "Vaccines for established cancer: overcoming the challenges posed by immune evasion" Nature Reviews (2016) 16(4):219-233.
Topper, M.J., et al., "Epigenetic Therapy Ties MYC Depletion to Reversing Immune Evasion and Treating Lung Cancer" Cell (2017) 171:1284-1300.
Bandopadhayay, P., et al., "BET Bromodomain Inhibition of MYC-Amplified Medulloblastoma" Clin. Cancer Res. (2014) 20(4):912-25.
Adeegbe, D.O., et al., "Synergistic Immunostimulatory Effects and Therapeutic Benefit of Combined Histone Deacetylase and Bromodomain Inhibition in Non-Small Cell Lung Cancer" Cancer Discovery (2017) 7(8):852-867.
Adeegbe, et al., "BET bromodomain inhibition synergizes with immune checkpoint blockade to facilitate anti-tumor response in a murine model of non-small cell lung cancer harboring activating KRAS mutation" J. Immunol. (2016) 196 (1_Supplement):74.10.
Attwell, et al., "The investigational drug ZEN-3694, a novel BET-bromodomain inhibitor, inhibits multiple tumor immune escape mechanisms and has the potential to combine with immunotherapies" Eur. J. Cancer (2016) 69(Supp 1):Poster P089.
Korkut, et al., "Perturbation biology nominates upstream-downstream drug combinations in RAF inhibitor resistant melanoma cells" eLife (2015) 4:e04640.
Wu, et al., "MYC oncogene is associated with suppression of tumor immunity and targeting Myc induces tumor cell immunogenicity for therapeutic whole cell vaccination" Journal for ImmunoTherapy of Cancer (2021) 9:e001388.
Mao, et al., "Immunogenicity of prostate cancer is augmented by BET bromodomain inhibition" Journal for Immuno Therapy of Cancer (2019) 7:277.
Croft, et al., "Kinetics of Antigen Expression and Epitope Presentation during Virus Infection" PLoS Pathog. (2013) 9 (1): e1003129.

(56) References Cited

OTHER PUBLICATIONS

Paretsky, et al., "Mutations Associated with Acquired Resistance to PD-1 Blockade in Melanoma" N. Engl. J. Med. (2016) 375:819-829.
Restifo, et al., "Loss of Functional Betar Micro globulin in Metastatic Melanomas From Five Patients Receiving Immunotherapy" J. Natl. Cancer Inst. (1996) 88:100-108.
Marty, et al., "MHC-I Genotype Restricts the Oncogenic Mutational Landscape" Cell (2017) 171(6):1272-1283.

* cited by examiner

IMMUNOGENIC COMPOSITION FOR THE TREATMENT OF CANCER

This application is a § 371 application of PCT/EP2018/076539, filed Sep. 28, 2018, which in turn claims priority to EP Application Serial No. 17194223.8, filed Sep. 29, 2017. The entire disclosure of each of the foregoing applications is incorporated by reference herein.

FIELD OF THE INVENTION

The invention relates to the field of immunotherapy, more in particular to a composition for use in the treatment of cancer. The invention also relates to a composition obtainable by such a method, such as a pharmaceutical composition.

BACKGROUND OF THE INVENTION

The recent years have seen a large increase in immunotherapeutic approaches for cancer, with notable clinical success being achieved by the use of antibodies blocking immune checkpoints molecules.[1] Highly encouraging results have also been obtained in cancer patients undergoing other types of immunotherapy, such as adoptive transfer of ex vivo activated T cells and various therapeutic vaccination strategies.[2-7]

Despite these substantial advances, many immunotherapies fail to induce clinical benefit in large groups of cancer patients. A major reason for this is that anti-tumor immunity is often rendered ineffective by immune evasion mechanisms employed by tumors. In this respect, a key underlying factor for poor clinical responses to immunotherapy is the intrinsic ability of many tumors to prevent recognition of cancer antigens by the immune system (Cavallo, De Giovanni, Nanni, Forni, & Lollini, 2011; Khan, Gregorie, & Tomasi, 2008; Landsberg et al., 2012; McGranahan et al., 2017; Munn & Mellor, 2013; Respa et al., 2011; Setiadi et al., 2008; van der Burg, Arens, Ossendorp, van Hall, & Melief, 2016; Woo et al., 2012; Zaretsky et al., 2016). Evidence indicates that these abilities, which can typically be caused by disruptions in interferon-gamma signaling or the antigen presentation machinery, may be acquired by tumors and can thereby often lead to delayed relapses in patients despite good initial responses and continuous immunotherapy.[8] Thus, there is a clear need for novel ways to improve the efficacy of cancer immunotherapies.

The use of autologous tumor cells as a potential tool in immune therapy has been described before, however so far such attempts were hardly successful since tumor cells failed to induce an adequate T-cell response.

SUMMARY OF THE INVENTION

The present invention aims at overcoming these problems, amongst others. Particularly, the invention aims at improving existing therapies or immunotherapies by providing a method which aims at using primary autologous tumor cell and treat these cells ex vivo or directly in vivo with an inhibitor of Bromodomain and Extra-Terminal domain proteins (BET inhibitor or BETi).

As discussed in detail below, the inventors have surprisingly discovered that BET inhibitors have numerous effects on tumor cells that are beneficial for therapeutic reasons. In particular, as shown in the accompanying Examples, BET inhibitors enhance interferon-gamma signaling, increase interferon-gamma-induced antigen presentation, suppress constitutive and interferon-gamma-induced HLA class II expression, suppress constitutive and interferon-gamma-induced indoleamine 2,3-dioxygenase (IDO) production, and suppress constitutive and interferon-gamma-induced PD-L1 expression, in tumor cells. The inventors' findings therefore provide an attractive way to improve the efficacy of cancer immunotherapy, by targeting tumor-intrinsic molecular pathways and enhancing their immunogenicity.

The present invention therefore provides new uses, methods and compositions for treating cancer based on the inventors' surprising findings regarding the effect of BET inhibitors on tumor cells. In some aspects, the invention provides the direct in vivo administration of BET inhibitors to particular sub-groups of patients with cancer. In further aspects, the invention provides approaches in which primary cancer cells or patient-derived cancer cell lines are exposed ex vivo to BET inhibitors to enhance their immunogenicity, thereby making these cells suitable for use as an immunogenic vehicle to promote anti-tumor immune responses, for example by autologous vaccination.

The invention therefore relates to an ex vivo method for obtaining a composition suitable for the treatment of cancer in a subject, comprising the steps of providing primary tumor cells derived from the subject or tumor cell lines derived from the subject, and ex vivo contacting the tumor cells with a BET inhibitor. Alternatively, the BET inhibitor can be administered in vivo to one or more tumor cell locations.

The invention also relates to a composition obtainable or obtained by such a method and their use in the treatment of cancer.

The invention also relates to the use of BET inhibitors to increase the expression and presentation of tumor-specific neo-antigens and/or tumor-associated antigens in one or more tumor cells.

The invention also relates to uses and methods for treating particular sub-groups of patients having cancer, in which the BET inhibitor is administered to such patients and enhances the (interferon-gamma-induced) expression and presentation of tumor-specific neo-antigens and/or tumor-associated antigens in one or more tumor cells, in one or more tumor cell locations, enhances interferon gamma signaling in one or more tumor cells, in one or more tumor cell locations, or suppresses in one or more tumor cells, in one or more tumor cell locations, the expression of proteins involved in immunosuppressive pathways, such as HLA class II, IDO, PD-L1 and CD73.

LEGEND TO THE FIGURES

FIG. 1. JQ1 differentially sensitizes melanoma cells for recognition by autologous TIL.

Top row: ANRU, ROAL, KADA and A375 tumor cells were cultured for 72 hours in the presence of JQ1 and/or IFNγ, washed, harvested and subsequently co-culture for another 24 hours with autologous tumor-infiltrating lymphocytes (TIL), and with allogeneic T cells for A375 cells. As indicated by IFNγ levels in the co-culture supernatants, determined by ELISA, T-cell recognition was strongly and significantly enhanced compared to DMSO-treated tumor cells by JQ1 alone or in combination with IFNγ, except for KADA. Second and third row: Histogram overlays of PD-L1 and HLA class I expression after 72 hour treatment with JQ1 and/or IFNγ, as determined by flow cytometry. Fourth and fifth row: Quantified expression of PD-L1 and HLA class I expression after 72 hour treatment with JQ1 and/or IFNγ, determined by flow cytometry, showing that enhanced recognition of tumor by TIL was not associated with any effects on PD-L1 expression, but seemed more in line with enhanced HLA class I induction by IFNγ in the presence of JQ1. Sixth row: Quantified expression of HLA class II after 72 hour treatment of ANRU, ROAL, KADA and A375 tumor cells with JQ1 and/or IFNγ, indicating that its induction by IFNγ can be suppressed in the presence of JQ1, though there is no clear relation with recognition by T cells.

FIG. 2. JQ1 enhances tumor recognition by TIL independently from PD-L1.

ANRU cells were cultured for 0, 12, 24, 48 and 72 hours in the presence of JQ1 and/or IFNγ, then washed, harvested and subsequently co-cultured for another 24 hours with autologous tumor-infiltrating lymphocytes (TIL) in the absence and presence of a blocking antibody for PD-L1. As indicated by IFNγ levels in the co-culture supernatants, determined by ELISA, TIL recognition was increasingly enhanced with longer treatment durations, as compared to DMSO-treated tumor cells, without any effect of the presence of an antibody blocking PD-L1.

FIG. 3. JQ1 potentiates IFNγ-induced activation of the antigen-presentation machinery.

(A) After treatment of ANRU, ROAL, KADA and A375 cells for 72 hours with JQ1 and/or IFNγ, mRNA expression levels were studied by qPCR of a range of molecules of the antigen-presentation machinery (APM). We found that JQ1 for nearly of these components potentiated their induction by IFNγ, the most pronounced effects being observed for HLA class I, beta-2 microglobulin (B2M), TAP1 and TAP2. (B) mRNA expression levels of APM components in untreated ANRU cells and ANRU cells treated for 12, 24, 48 and 72 with 0.4 µM JQ1 and/or 25 ng/ml IFNγ, showing clearly potentiated induction of APM components by IFNγ in the presence of JQ1 at all time points. (C) Western blot analysis of ANRU, ROAL, KADA and A375 cells after 72 hour treatment with JQ1 and/or IFNγ also indicated enhanced induction of APM components by IFNγ in the presence of JQ1 at the protein level. This was most apparent for HLA class I heavy chain, and overall was most clearly seen in A375 cells.

FIG. 4. JQ1 enhances recognition of tumor-associated and mutant antigens by autologous tumor-infiltrating lymphocytes.

ANRU tumor cells were treated with 0.4 µM JQ1 and/or 25 ng/ml IFNγ for 72 hours, and were subsequently co-cultured with autologous tumor-infiltrating lymphocytes (TIL) sorted for their specificity towards either the tumor-associated antigen MART-1, or two different tumor-specific mutant antigens, ETV6.9 and NUP210 (designated pos). Tumor cells were also co-cultured with unsorted TIL, and TIL without specificity for the aforementioned tumor antigens (designated 'neg'). As indicated by IFNγ levels in co-culture supernatants, measured by ELISA, JQ1 improved recognition by all three TIL populations with specificity towards the indicated antigens, to an extent that was either similar to or stronger than what was observed after pretreatment by IFNγ alone or DMSO.

FIG. 5. Dose-dependent enhancement of HLA class I induction by IFNγ in the presence of JQ1, I-BET151 and I-BET762.

Cells were treated for 72 hours with the BET inhibitors JQ1, I-BET151 or I-BET762, either alone or in combination with IFNγ. HLA class I induction by IFNγ, as determined by flow cytometry, was clearly dose-dependently increased when used in combination with all these BETi.

FIG. 6. JQ1 enhances IFNγ-induced HLA class I expression and suppression constitutive and IFNγ-induced of multiple immune checkpoint molecules.

Quantified expression of PD-L1, HLA class I, HLA class II and IDO after 72 hour treatment with JQ1 and/or IFNγ, determined by flow cytometry, showing that enhanced recognition of early-passage melanoma cell lines by autologous TIL, as depicted in FIG. 1, coincides with enhanced HLA class I induction by IFNγ in the presence of JQ1 and, in the case of ANRU and ROAL, without any effects on PD-L1. Both constitutive and IFNγ-induced HLA class II expression are clearly suppressed by JQ1 as well, while it also suppresses IFNγ-induced IDO expression.

FIG. 7. JQ1 potentiates IFNγ-induced activation of the antigen-presentation machinery and enhances expression of key proteins in the IFNγ-signaling pathway.

Quantified expression of PD-L1, HLA class I, HLA class II and CD73 after 72 hour treatment with JQ1 and/or IFNγ, determined by flow cytometry on commercially available human tumor cell lines of various origins. The data indicate that JQ1 enhances HLA class I induction by IFNγ on A549 (lung carcinoma), HCT116 (colon carcinoma) and HeLa (cervical carcinoma) cells, while it JQ1 suppresses CD73 induction by IFNγ.

FIG. 8. JQ1 potentiates IFNγ-induced activation of the antigen-presentation machinery and enhances expression of key proteins in the IFNγ-signaling pathway.

(A) After treatment of ANRU, ROAL, KADA and A375 cells for 72 hours with JQ1 and/or IFNγ, mRNA expression levels were studied by qPCR of a range of molecules of the antigen-presentation machinery (APM). We found that JQ1 for nearly of these components potentiated their induction by IFNγ, the most pronounced effects being observed for HLA class I, beta-2 microglobulin (B2M), TAP1, TAP2 and LMP10.

(B) mRNA expression levels, measured by RT-qPCR, in ANRU, ROAL and A375 cells of STAT1 and JAK1, two proteins crucially involved in signaling downstream of IFNγ ligation to its cognate receptor. The data indicate that JQ1 strongly enhances induction of STAT1 by IFNγ, while JQ1 by itself and in combination consistently increases JAK1 expression.

FIG. 9. Analysis of protein expression changes by mass spectrometry in lysates of ANRU cells that were incubated for 24 hours with JQ1 and/or IFNγ. Depicted are fold changes versus expression in control treatment with an amount of DMSO that is equivalent to the amount present in the other treatment conditions.

FIG. 10. Analysis of protein expression changes by mass spectrometry in lysates of ANRU cells that were incubated for 24 hours with JQ1 and/or IFNγ.

(A) Gene set enrichment analysis on proteins detected by mass spectrometry ANRU cells after 24 hours of treatment with IFNγ and/or JQ1. Depicted are significantly enriched pathways, ranked according to their p-value, that were identified by analysis on the subset of proteins that was induced by IFNγ, but whose induction was either potentiated or suppressed in case IFNγ treatment was performed in the presence of JQ1. In red the pathway with proteins whose induction by IFNγ was mostly suppressed when IFNγ treatment was done in combination with JQ1.

(B) Network analysis of the subset of proteins used also for gene set enrichment analysis in FIG. 9A. In red the node with proteins whose induction by IFNγ was mostly suppressed when IFNγ treatment was done in combination with JQ1.

FIG. 11. MYC expression is downregulated by 72 hours treatment with JQ1 alone or in combination with IFNγ, as indicated by western blot analysis.

FIG. 12. JQ1-induced enhancement of tumor recognition by TIL is independent from PD-L1, but abrogated by blockade of HLA class I ANRU cells were cultured for 0, 12, 24, 48 and 72 hours in the presence of JQ1 and/or IFNγ, then washed, harvested and subsequently co-cultured for another 24 hours with autologous tumor-infiltrating lymphocytes (TIL) in the absence and presence of a blocking antibody for PD-L1. As indicated by IFNγ levels in the co-culture supernatants, determined by ELISA, TIL recognition was increasingly enhanced with longer treatment durations, as compared to DMSO-treated tumor cells, without any effect of the presence of an antibody blocking PD-L1. At the same time, blocking HLA class I almost completely abrogated tumor recognition by TIL.

DETAILED DESCRIPTION OF THE INVENTION

This invention addresses the problem that certain tumors cannot efficiently induce an immune response. This problem is overcome by the present invention wherein a patient is treated with a BET inhibitor or wherein a primary tumor cell is isolated from the tumor, or a tumor cell line is derived from the tumor, and incubated in vitro or ex vivo with a BET inhibitor. Such a composition can then induce an effective T-cell immune response in the donor of the primary tumor cells when administered to that subject. It will be appreciated by those skilled in the art that therapeutic immune responses can be induced by vaccination against various tumor antigens, even though initially (i.e. before treatment) the target antigen in untreated individuals is not recognized, or at least not recognized efficiently enough to elicit a protective anti-tumor immunity. This is supported by observation of the so-called abscopal effect, which is the phenomenon that localized treatment of a tumor in metastatic cancer not only lead to regression of the treated tumor, but also of tumors outside the scope of the localized treatment. This effect has been described after intratumoral application of a variety of immunotherapies, indicating that activation of tumor antigen-specific T cells locally can lead to systemic T cell-mediated tumor eradication (Fransen, Sluijter, Morreau, Arens, & Melief, 2011; Fransen, van der Sluis, Ossendorp, Arens, & Melief, 2013; Ishihara et al., 2017; Kim et al., 2012; Marabelle, Tselikas, de Baere, & Houot, 2017; Sagiv-Barfi et al., 2018).

Such treatment can greatly improve the immune response to tumor cells and provides a useful tool to replace or be used in combination with existing immunotherapies. Several advantages are associated with using such method, as it has surprisingly been found that BET inhibitors are able to greatly induce antigen presentation in tumor cells ex vivo, especially when combined with concurrent or subsequent exposure to interferon-gamma.

Several advantages are also associated with using such method when compared to systemic administration of BET inhibitors to a patient. As the method of the invention does not require the systemic or local administration of BET inhibitors to a subject, it eliminates any potential problems associated with toxicity or adverse responses to the inhibitors, as well the problem that the inhibitors may not reach the tumor effectively. At the same time, in vivo administration of BETi orally and/or intravenously and/or intratumorally and/or in any other way is still of high relevance as it may enhance the efficacy of other immunotherapies used to treat the patient, such as checkpoint blockade or adoptive transfer of TCR transgenic T cells or CAR T cells.

Therefore, the invention relates to an ex vivo method for obtaining a composition suitable for the treatment of cancer in a subject, comprising the steps of providing primary tumor cells derived from the subject, or a tumor cell line derived from the tumor, and ex vivo contacting the tumor cells with a BET inhibitor.

Treating the tumor cells derived from a subject, or the tumor cell line, in the way as described above, strongly induces antigen presentation of the autologous tumor cells. When such treated cells are administered to the subject, a tumor specific T-cell response is induced, making such cells very suitable to be used in a subject to elicit a tumor specific immune response.

It will be appreciated that the inventors' surprising finding that BET inhibitors are able to greatly induce antigen presentation in tumor cells is not only applicable to primary tumor cells derived from the subject, but can be used to induce antigen presentation in tumor cell lines, such as tumor cell lines derived from the subject or (commercially available) allogeneic cell lines that may express shared (neo)antigens in the context of the same HLA class I serotype or haplotype. Accordingly, where the present invention refers to methods, uses and/or compositions involving primary tumor cells derived from a subject, we also include tumor cell lines derived from the subject and/or HLA matched allogeneic cell lines that express targetable tumor antigens.

BET inhibitors are a class of drugs with anti-cancer, immunosuppressive, and other effects in clinical trials and are widely used in research. These molecules reversibly bind the bromodomains of Bromodomain and Extra-Terminal motif (BET) proteins, such as BRD2, BRD3, BRD4, and BRDT. They are thought to prevent protein-protein interaction between BET proteins and acetylated histones and transcription factors. Since 2010 a number of molecules have been described that are capable of targeting BET bromodomains.

Tumor cells, like all cells, use the HLA class I complex to present antigens on the surface. As mutations accumulate in the tumor cells, some of these antigens will include neo-antigens. Such neo-antigens can be detected as non-self by T-cells, such as CD8+ T-cells, resulting in an immune response targeted specifically at the tumor cells.

Tumors are known to develop ways to avoid such immune responses; one such methods is by upregulating PD-L1, which suppresses HLA-mediated T-cell activation.

Small-molecular inhibitors of the family of Bromodomain and extraterminal domain (BET) proteins are highly interesting in this respect, as they were recently found to strongly suppress constitutive and inducible PD-L1 expression in various tumor mouse models, as well as on various human cancer cell lines.[9,10] Importantly, inhibition of BET proteins combined with an anti-PD-1 checkpoint blockade led to synergistic responses in mice bearing Myc-driven lymphomas.[10]

Physiologically, BET proteins form a class of epigenetic 'readers' that use bromodomain (BRD) modules to bind acetylated lysines on DNA histone tails, thereby acting as a scaffold for transcription factors and other nuclear proteins to regulate gene transcription. In this way they control the expression of key oncogenes, such as c-Myc, and various anti-apoptotic proteins.[11]

BET inhibitors (BETi) are a relatively new class of anti-cancer drugs that were originally developed for use as a targeted therapy to inhibit tumor growth. These effects were described first for the BETi JQ1 in NUT midline carcinoma, a rare malignancy characterized by overexpression of the BET protein BRD4, one of the main BETi targets, along with BRD2 and BRD3.[12]

Later studies reported comparable effects of JQ1 and the BET inhibitors I-BET151 and I-BET762 in several other types of cancer, including Myc-driven hematological malignancies, melanoma and neuroblastoma.[13-15] Brd4 is thought to be the main target in all these studies, while the effects on Myc-driven tumors are also attributed to Myc-downregulation.[16,17] As a consequence of these results, various BET inhibitors are now in early clinical development as anti-proliferative agents for both solid tumors and hematological cancers. Thus far, this has indicated that BET inhibitors can indeed exert anti-tumor activity with manageable and reversible toxicity in patients.[18]

Despite the promising results obtained with BET inhibitors as a potential treatment for cancer, several disadvantages still need to be overcome. For example, systemic administration of a BET inhibitor may be toxic, or result in unwanted effects such as autoimmune responses. Further, depending on the tumor type BET inhibitors may not reach the tumor in sufficient amounts to exert their effect. Lastly, it is known that not all tumor types respond to treatment with BET inhibitors.

It has now been found that independently of reduction of PD-L1 expression, BET inhibitors result in increased antigen presentation, especially in combination with concurrent or subsequent exposure to interferon-gamma, in tumor cells that were isolated from their natural environment. In particular, and as demonstrated in the accompanying Examples, the inventors have found that BET inhibitors have the following effects on tumor cells: increased interferon-gamma signalling; increased antigen presentation (for example, increased interferon-gamma-induced) antigen presentation); suppressed constitutive and interferon-gamma-induced HLA class II expression; suppressed constitutive and interferon-gamma-induced indoleamine 2,3-dioxygenase (IDO) production; suppressed constitutive and interferon-gamma-induced PD-L1 expression; and suppressed constitutive and interferon-gamma-induced CD73 expression. Based on this finding, new and improved treatment strategies were developed by the inventors making use of the previously unknown effect of BET inhibitors.

To this effect, a method is developed of isolating primary tumor cells from a subject with cancer, and treating those primary tumor cells ex vivo with a BET inhibitor. In this way, primary tumor cells with strongly increased antigen presentation are obtained. Such cells are useful as they may be administered to the subject to generate an effective tumor-specific T-cell response.

To the best of our knowledge, ex vivo treatment of primary tumor cells with a BET inhibitor to obtain a composition for use in the treatment of cancer has not been previously described.

It has now surprisingly been found that isolating tumor cells from a patient with cancer and treating those cells with a BET inhibitor greatly increases the antigen presentation of those cells, particularly tumor specific neo-antigen presentation. Therefore, these cells are very suitable as vehicles for immunotherapy in said patient to induce a tumor cell specific immune response, as the treated cells are derived from the tumor and thereby trigger the immune system to respond to the tumor cells.

Such effect would not be observed if allogeneic cells would be used. As the effects of BET inhibitors were previously considered to be mediated by reduced expression of PD-L1 only, use of BET inhibitors to treat autologous cells derived from primary tumor cells ex vivo has not been considered or suggested so far.

The data presented here demonstrates that the effect of increased antigen presentation is independent of PD-L1 expression.

Now that we have found that BET inhibition can sensitize tumor cells for recognition by autologous and allogeneic T cells ex vivo, through enhanced activation of the antigen-presentation machinery (for example, caused by interferon gamma exposure), irrespective of any effects on PD-L1 regulation, it opens the way to a more effective treatment wherein a primary tumor cell is isolated from a subject, contacted with a BET inhibitor and administered back to the subject and/or used to expand autologous T cells ex vivo, for ensuing therapy by adoptive transfer for example.

Here we show that BET inhibition can sensitize human melanoma and other cancer cells for recognition by autologous T cells. Importantly, BET inhibition induces this effect not only by suppressing PD-L1, but also by enhancing interferon-gamma-induced activation of the antigen-presentation machinery.

Hence, the invention also relates to a method as described above, wherein the tumor cells are contacted with an immunostimulatory compound and the BET inhibitor either simultaneously or sequentially. Particularly preferred immunostimulatory compounds are: interferon gamma, interferon alpha, agonists of the stimulator of interferon genes (STING) pathway, inhibitors of cyclin-dependent 4 and/or 6 (e.g. palbociclib), DNA methyltransferase inhibitors or histone deacetylase inhibitors.

We show that these mechanisms strongly sensitize patient-derived melanoma cells to be recognized by autologous tumor-infiltrating lymphocytes (TIL). Moreover, the effects of BET inhibition on PD-L1 and antigen-presentation were induced partly or completely independently from Myc.

BET inhibitors were shown to suppress constitutive PD-L1 expression and interferon-gamma-induced PD-L1 expression in various types of cancer, including ovarian cancer and B-cell lymphoma. Moreover, inhibition of tumor outgrowth was shown to require an intact immune system in mice.[10]. Here, we show that inhibition of BRD4 suppresses PD-L1 expression.

In the context of the invention, the term "ex vivo" is to be understood as taking place outside of the subject from which the tumor cells are derived from. The subject may be an animal or a human, the subject may also be a non-human mammal.

The subject may have a cancer or a carcinoma, a solid tumor or a hematological cancer. As used herein, the term "patient" refers to a subject undergoing treatment or examination by a medical or veterinary professional.

Primary tumor cells are provided by identifying a subject with cancer and removing a subset or a substantial part, or even all of the tumor cells from the subject. Methods for diagnosing a subject with cancer, identifying the tumor in said subject and removing part or all of the tumor are generally known to the skilled person. Non limiting examples of suitable methods for isolating tumor cells from a subject are by surgery, biopsy or blood withdrawal. The skilled person will be aware of other methods of obtaining tumor cells and the most suitable method for doing so, depending on the tumor type.

Once tumor cells are isolated from the subject they may optionally be separated from impurities such as non-tumor cells or extracellular material. Preferably the tumor cells are kept in a suitable culture medium once isolated from the subject, however it is also envisioned in the invention that the tumor cells are stored for later use, for example by freezing the cells or keeping the cells in a suitable storage medium.

In the context of the invention, the term primary tumor cells should be interpreted as cells that are isolated from a tumor in a subject and prepared for ex vivo treatment without substantially modifying the tumor cells, such as modifying the genome to generate immortal cell lines.

It is to be understood that the primary tumor cells may be expanded after isolation from the subject and before the step of contacting them with the BET inhibitor. Methods for expanding primary tumor cells ex vivo and in vitro are well known to the skilled person.

BET inhibitors are known to the skilled person to be able to block, inhibit or down regulate the function of BET motif containing proteins. Non-limiting examples of BET domain containing proteins are the BRD2, BRD3, BRD4, and BRDT proteins. BET inhibitors have been described in the art and are well known to the skilled person. When used herein therefore the term BET inhibitor refers to any compound, molecule or composition capable of blocking, inhibiting or down regulating BET domain containing proteins. Non limiting examples of classes of BET inhibitors according to the invention are small molecules, antisense nucleotides and antibodies.

Small molecule BET inhibitors are generally able to reversibly bind the bromodomains of Bromodomain and Extra-Terminal motif (BET) proteins, and prevent protein-protein interaction between BET proteins and acetylated histones and transcription factors.

Preferred examples of small molecule BET inhibitors according to the invention are BET inhibitors selected from the group consisting of JQ1, MK-8628, BMS-986158, INCB54329, ABBV-075, CPI-0610, FT-1101, GS-5829, GSK525762, PLX51107, Ten-010, OTX-015, CPI-0610, 3-methyl-1,2,3,4-tetrahydroquinazolin-2-ones, 2-thiazolidinones, CPI-203, I-BET762 (GSK525762A), I-BET151 (GSK1210151A), and RVX208.

Specially preferred are BET inhibitors selected from the group consisting of JQ1, I-BET151 (GSK1210151A), and I-BET762 (GSK525762A).

It is further understood that the invention also includes chemical modifications of the small molecule BET inhibitors as described herein. In a more preferred embodiment of the invention the small molecule BET inhibitor is selected from the group consisting of JQ1, MK-8628, BMS-986158, INCB54329, ABBV-075, CPI-0610, FT-1101, GS-5829, GSK525762, PLX51107, Ten-010, OTX-015, and CPI-0610. However it is further envisioned that the BET inhibitor may be a novel or previously unknown small molecule BET inhibitor. BET inhibitory activity of a compound can easily be assessed by the skilled person, for example using pull down techniques with a bromodomain and extraterminal motif protein and detection of binding of the compound to the bromodomain and extraterminal motif protein.

Preferably the small molecule BET inhibitor is provided to the tumor cells ex vivo for a time sufficient to allow the cells to express neo-antigens on their surface, such as for instance at least 6 hours, more preferable at least 8 hours, more preferably at least 10 hours, even more preferably at least 12, even more preferably at least 18 hours, even more preferably at least 24 most preferably at least 30 hours.

Alternatively, the BET inhibitor according to the invention may be an antisense gene silencer, such as but not limited to siRNA, miRNA, CRISPRs and TALENs. An antisense oligonucleotide may comprise deoxyribonucleic acids and/or ribonucleic acids and/or artificial nucleotides such as a nucleotide analogue, the nucleotides may comprise natural bases, adenine, cytosine, guanine, thymine, uracil, or non-natural bases. The oligonucleotide may also comprise a modified backbone. Non-limiting examples of nucleic acid analogous with a modified backbone include peptide nucleic acid (PNA), Morpholino and locked nucleic acid (LNA), as well as glycol nucleic acid (GNA) and threose nucleic acid (TNA). The skilled person will be aware of protocols and design strategies in order to effectively achieve downregulation of BET domain containing proteins.

In the context of the invention the term composition suitable for the treatment of cancer in a subject, should be interpreted as a composition capable of triggering an anti-tumor immune response when administered to the subject. Preferably the anti-tumor response is the induction of a tumor specific T-cell response. Preferably such response is induced be the increased antigen presentation on the tumor cells of the composition according to the invention.

Ex vivo contacting the primary tumor cells with a BET inhibitor is to be understood as providing the BET inhibitor to the cells in an amount and for a time period sufficient to induce a response, the response preferably being increased antigen presentation. Preferably the BET inhibitor is provided to the tumor cells ex vivo in a concentration between 1 and 10.000 times the IC50 value, preferably between 5 and 2000 times the IC50 value, more preferably between 10 and 1000 times the IC50 value, most preferably the concentration is between 25 and 250 times the IC50 value of said BET inhibitor for the BET domain containing protein.

In the case of JQ1, the IC50 values for the first and second bromodomain are 77 nM and 33 nM respectively, therefore, the concentration of JQ1 when used as a BET inhibitor in the method of the invention is preferably between 50 nM and 500 µM, more preferably between 250 nM and 100 µM, more preferably between 500 nM and 50 µM, most preferably the concentration of JQ1 when used in the method according to the invention is between 1 µM and 10 µM. Even more preferably the concentration is between 0.1 µM and 10 µM.

It is to be understood that the concentration or duration of treatment with the BET inhibitor may be adjusted for each individual BET inhibitor, the skilled person will be aware that he may do so for example using the individual IC50 or Ki values as a starting point to adjust the concentration of the BET inhibitor used in the method of the invention.

In the context of the invention, the term tumor specific T-cell response should be interpreted as a T-cell mediated immune response in vivo specifically directed at the tumor cells. As treatment of BET inhibitors results in increased antigen presentation in the tumor cells in vitro or ex vivo, this results in an increased presentation of tumor specific antigens. Such tumor specific antigens have been demonstrated to elicit an immune response which is mediated by T-cells recognizing non-native tumor specific antigens.

Preferably the method of the invention is for providing a composition suitable for treating cancer in a subject wherein the cancer is selected from the list consisting of Acute Lymphoblastic Leukemia (ALL), Acute Myeloid Leukemia (AML), Adrenocortical Carcinoma, AIDS-Related Cancers Kaposi Sarcoma, AIDS-Related Lymphoma, Primary CNS Lymphoma, Anal Cancer, Appendix Cancer, Astrocytomas, Atypical Teratoid/Rhabdoid Tumor, Basal Cell Carcinoma of the Skin, Bile Duct Cancer, Bladder Cancer, Bone Cancer, Brain Tumors, Breast Cancer, Bronchial Tumors, Burkitt Lymphoma, Carcinoid Tumor, Childhood Carcinoid Tumors, Carcinoma of Unknown Primary, Cardiac (Heart) Tumors, Central Nervous System Atypical Teratoid/Rhabdoid Tumor, Embryonal Tumors, Germ Cell Tumor, Primary CNS Lymphoma, Cervical Cancer, Cholangiocarcinoma, Chordoma, Chronic Lymphocytic Leukemia (CLL), Chronic Myelogenous Leukemia (CML), Chronic Myeloproliferative Neoplasms, Colorectal Cancer, Craniopharyngioma, Cutaneous T-Cell Lymphoma, Ductal Carcinoma In Situ (DCIS), Embryonal Tumors, Endometrial Cancer, Ependymoma, Esophageal Cancer, Esthesioneuroblastoma, Ewing Sarcoma, Childhood Extracranial Germ Cell Tumor, Extragonadal Germ Cell Tumor, Eye Cancer, Intraocular Melanoma, Retinoblastoma, Fallopian Tube Cancer, Fibrous Histiocytoma of Bone, Gallbladder Cancer, Gastric (Stomach) Cancer, Gastrointestinal Carcinoid Tumor, Gastrointestinal Stromal Tumors (GIST), Germ Cell Tumors, Childhood Extracranial Germ Cell Tumors, Extragonadal Germ Cell Tumors, Ovarian Germ Cell Tumors, Testicular Cancer, Gestational Trophoblastic Disease, Hairy Cell Leukemia, Head and Neck Cancer, Heart Tumors, Hepatocellular (Liver) Cancer, Langerhans Cell Histiocytosis, Hodgkin Lymphoma, Hypopharyngeal Cancer, Intraocular Melanoma, Islet Cell Tumors, Pancreatic Neuroendocrine Tumors, Kaposi Sarcoma (Soft Tissue Sarcoma), Kidney (Renal Cell) Cancer, Langerhans Cell Histiocytosis, Laryngeal Cancer, Leukemia, Lip and Oral Cavity Cancer, Liver Cancer, Lung Cancer (Non-Small Cell and Small Cell), Lymphoma, Male Breast Cancer, Malignant Fibrous Histiocytoma of Bone and Osteosarcoma, Melanoma, Merkel Cell Carcinoma, Mesothelioma, Metastatic Cancer, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasms, Mycosis Fungoides (Lymphoma), Myelodysplastic Syndromes, Chronic Myelogenous Leukemia (CML), Acute Myeloid Leukemia (AML), Chronic Myeloproliferative Neoplasms, Nasal Cavity and Paranasal Sinus Cancer, Nasopharyngeal Cancer, Neurobiastoma, Non-Hodgkin Lymphoma, Non-Small Cell Lung Cancer, Oral Cancer, Lip and Oral Cavity Cancer, Oropharyngeal Cancer, Osteosarcoma and Malignant Fibrous Histiocytoma of Bone, Ovarian Cancer, Pancreatic Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Pregnancy and Breast Cancer, Primary Central Nervous System (CNS) Lymphoma, Primary Peritoneal Cancer, Prostate Cancer, Rectal Cancer, Recurrent Cancer, Renal Cell (Kidney) Cancer, Retinoblastoma, Rhabdomyosarcoma, Childhood (Soft Tissue Sarcoma), Salivary Gland Cancer (Head and Neck Cancer), Sarcoma, Childhood Vascular Tumors (Soft Tissue Sarcoma), Ewing Sarcoma (Bone Cancer), Kaposi Sarcoma (Soft Tissue Sarcoma), Osteosarcoma (Bone Cancer), Uterine Sarcoma, Sézary Syndrome (Lymphoma), Skin Cancer, Small Cell Lung Cancer, Small Intestine Cancer, Soft Tissue Sarcoma, Squamous Cell Carcinoma of the Skin, Squamous Neck Cancer, Stomach (Gastric) Cancer, T-Cell Lymphoma, Testicular Cancer, Throat Cancer, Nasopharyngeal Cancer, Oropharyngeal Cancer, Hypopharyngeal Cancer, Thymoma and Thymic Carcinoma, Thyroid Cancer, Transitional Cell Cancer of the Renal Pelvis and Ureter, Ureter and Renal Pelvis, Transitional Cell Cancer, Urethral Cancer, EndometrialUterine Cancer, Uterine Sarcoma, Vaginal Cancer, Vascular Tumors (Soft Tissue Sarcoma), Vulvar Cancer, and Wilms Tumor.

It has been described in the art that not all tumors respond to treatment with BET inhibitors. It has now surprisingly be found that at least some tumors can be made responsive to the effects of BET inhibitors by co-stimulation of the tumor cells with Interferon gamma (IFNγ). Therefore, the ex vivo treatment of primary tumor cells with both BET inhibitors and IFNγ will result in increased antigen presentation in tumor cells that would otherwise be non-responsive to treatment with BET inhibitors alone. Therefore responsive cells can now be successfully used in a subject, when administered, to invoke a tumor specific T-cell response.

Hence, the invention also relates to a method as described above wherein the tumor cells are contacted with interferon gamma and the BET inhibitor either simultaneously or sequentially.

The simultaneous or sequential treatment with a BET inhibitor and gamma interferon has the additional advantage that the immune response is synergistically increased due to the synergistic increase of the antigen presentation on the autologous tumor cells. Therefore, treating tumor cells derived from a subject with BET inhibitors and IFNγ will result in a synergistically stronger tumor specific T-cell response when administered to the subject, as compared to treating the tumor cells with BET inhibitors or IFNγ alone.

In order to effectively exploit the method according to the invention, care has to be taken that the composition is not tumorigenic when administered to the subject.

Hence, the invention relates to a method as described above, wherein the composition is treated to prevent it from being tumorigenic in vivo before administering it to the subject.

Preferably therefore the composition comprising the primary tumor cells is treated in such a way that the cells contained in the composition cannot proliferate when administered to a subject in vivo. Examples of such treatment method are subjecting the cells to ionizing radiation, or subjecting the cells to mitotic inhibitors or cell cycle inhibitors, but other methods are known to the skilled person.

In a preferred embodiment of the invention, a method is provided wherein the composition is treated to prevent it from being tumorigenic in vivo by subjecting them to ionizing radiation. Preferably, the cells are subjected to at least 20 Gy, more preferably to at least 30 Gy, even more preferably at least 40 Gy, most preferably 50 Gy or more.

In an even further preferred embodiment of the invention, a method is provided wherein the method additionally comprises a step of ex vivo contacting the tumor cells with T-cells or dendritic cells obtained from the subject.

It is envisioned that the tumor cells treated according to the invention may be used for ex vivo expansion of T-cells (such as autologous T-cells) or dendritic cells, or to promote presentation of tumor antigens on dendritic cells. An advantage of this preferred method is that the T-cells or dendritic cells are activated in the composition and the method can therefore be used for treating cancer in the subject.

This method can also be used to generate T-cells and/or dendritic cells suitable for immunotherapy of a patient, or it can also be used to obtain a combination of tumor cells and/or T cells and/or dendritic cells suitable for the immunotherapy of cancer.

Therefore, in a further preferred embodiment of the invention, an ex vivo method is provided for obtaining a composition suitable for the treatment of cancer in a subject, wherein the method additionally comprises a step of ex vivo contacting the tumor cells with T-cells or dendritic cells obtained from the subject, and wherein the composition comprises T-cells, ex vivo expanded T-cells, or dendritic cells or a combination thereof, ex vivo treated with a BET inhibitor. Methods of expanding T cells are known in the art and exemplified in example 2.

The method according to the invention may be particularly advantageous for tumor cells that are negative for HLA (such as HLA class I) or PD-L1 or have low or no expression of HLA or PD-L1. In the context of the invention, the term "HLA negative or HLA class I negative or PD-L1 negative" should be interpreted as that the expression of HLA, HLA class I or PD-L1 (for example, when using immunostaining with an antibody that specifically recognizes these proteins, for example to perform immunohistochemistry or flow cytometry), is not upregulated and/or is not detectable.

In an embodiment, a tumor is considered to be HLA-negative or PD-L1-negative if the expression level does not significantly exceed that of non-tumor cells or of a normal tumor cell.

The expression may refer to mRNA levels or protein levels.

The presence of tumors that are PD-L1 positive is not a prerequisite for a patient to be eligible, as BETi can also enhance immunogenicity of PD-L1 negative tumors.

Hence, in an even further preferred embodiment of the invention, a method is provided wherein the tumor cells are HLA-negative tumor cells and/or PD-L1-negative tumor cells.

Additionally, the methods and uses of the invention may be particularly advantageous for patients having tumors with disrupted or poorly functioning molecular signaling downstream of the IFN-gamma receptor, and/or patients having tumors with high constitutive or IFN-gamma-induced expression of indoleamine 2,3-dioxygenase, and/or HLA class II and/or PD-L1.

It is envisioned that the method according to the invention may be used to obtain a composition suitable for the treatment of cancer, wherein the cancer is a solid tumor or a hematological cancer. Preferably, the cancer is a melanoma.

Solid tumors are also referred to as neoplasms and encompass the vast majority of tumor types, typically all tumors that are not considered hematological cancers. Hematological cancers are also known to the skilled person as tumors of the hematopoietic and lymphoid tissues, and comprise leukemias, lymphomas and myelomas.

In a more preferred embodiment of the invention, a method is provided wherein the cancer is melanoma.

In an even further preferred embodiment of the invention, a method is provided wherein the tumor cells in step a) are grown to organoids.

It is commonly known in the art that not all primary tumor cells are easily kept in culture ex vivo. One way to overcome this is to grow organoids from the primary tumor cells to establish a stable cell culture. Such organoids then can be treated with the BET inhibitors according to the method of the invention. Protocols for growing organoids from tumor cells are known to the skilled person and have been extensively described by Hans Clevers and Ton Logtenberg of the Hubrecht laboratory in Utrecht, the Netherlands.

In a further aspect of the invention, a composition is provided obtainable by a method according to the invention.

In a further preferred embodiment of the invention, a composition is provided obtained by a method according to the invention.

In a further aspect of the invention, a pharmaceutical composition is provided comprising the composition as described above and a pharmaceutically acceptable carrier or excipient.

Such compositions are characterized by an increased expression and presentation of tumor-specific neoantigens wherein the term "increased" refers to the level of expression and presentation of tumor-specific neoantigens as compared to normal, non-tumor cells and/or non-treated tumor cells in vivo or ex vivo.

In a further aspect, the invention provides a composition or a pharmaceutical composition of the invention for use in medicine.

In a further aspect, the invention provides a composition for use in the treatment of cancer wherein the treatment comprises administering of the composition to a subject, preferably wherein said administering comprises intradermal, subcutaneous, intramuscular, intravenous, or intratumoral administration or a combination thereof.

In an alternative embodiment the invention provides a method for treating cancer comprising administering of the composition to a subject wherein said administering preferably comprises intradermal, subcutaneous, intramuscular, intravenous, or intratumoral administration or a combination thereof.

In another alternative embodiment the invention provides the use of the composition according to the invention in the manufacture of a medicament for the treatment of cancer.

In a further preferred embodiment the invention provides a composition for use in the treatment of cancer, wherein the treatment as described above is combined with the systemic or localized administration in vivo or ex vivo of a drug selected from the group consisting of immunomodulatory compound, angiogenesis inhibitors, chemotherapeutics or c-Myc downregulation, preferably wherein the drug is an immunomodulatory compound selected from the group consisting of BET inhibitors, immunostimulatory cytokines, natural, endogenous or synthetic ligands of Toll like receptors, ligands of other immunostimulatory receptors, modulators of immune checkpoints, or agonistic modulators, epigenetic drugs (e.g. HDAC inhibitors and DNMT inhibitors) or compounds for targeted therapy (e.g. BRAF inhibitors and CDK4/6 inhibitors).

Non limiting examples of chemotherapeutics include: Alkylating agents, Anthracyclines, Cytoskeletal disruptors (Taxanes), Epothilones, Histone Deacetylase Inhibitors, Inhibitors of Topoisomerase I, Inhibitors of Topoisomerase II, Kinase inhibitors, Nucleotide analogs and precursor analogs, Peptide antibiotics, Platinum-based agents, Retinoids, Vinca alkaloids and derivatives, Non limiting methods to inhibit or downregulate c-Myc include using small-molecular compounds, RNA interference, or Antibodies.

Non limiting examples of immunostimulatory cytokines according to the invention are type I and II interferons: IFN-alpha, IFN-beta, IFN-gamma, IL-2, TNFα, GM-CSF, and Gamma C family of cytokines, e.g. IL-2, IL-7, IL-15 and IL-35.

Non limiting examples of natural, endogenous or synthetic ligands of toll-like receptors include natural, endogenous or synthetic ligands for:
TLR1 (e.g. triacylated lipopeptides, Pam3Cys)
TLR2 (e.g. Lipopolysaccharide, Heat Killed *Listeria monocytogenes*)
TLR3 (e.g. poly I:C)
TLR4 (e.g. Lipopolysaccharide, MPLA)
TLR5 (e.g. Flagellin)
TLR6 (e.g. FSL1)
TLR7 (e.g. imiquimod)
TLR8 (e.g. R848)
TLR9 (e.g. CpG-oligonucleotides)
TLR10

Any TLR agonist based on attenuated and/or fragmented viruses or bacteria

Any endogenous ligand (e.g. heat-shock proteins)

Non limiting examples of ligands of other immunostimulatory receptors include natural, endogenous or synthetic ligands for:

Receptor for advanced glycation endproducts (RAGE)

Stimulator of interferon genes (STING)

Non limiting examples of modulators of immune checkpoints may be selected from the group consisting of: CTLA-4, PD-1, PDL-1, PDL-2, TIM3, LAG3, B7-H3, B7-H4, BTLA, GAL9, and A2aR. The modulators can be a peptide, antibody, interfering RNA, or small molecule. In some cases, the immune modulator is a monoclonal antibody, or an Ig fusion protein.

Non limiting examples of agonistic modulators include modulators directed to a stimulatory immune molecule, e.g. 4-IBB (CD137), CD137L, OX40, OX40L, ICOS, CD40, CD40L, CD70, CD27, CD28, CD80, CD86, B7RP1, or HVEM. The modulators can be a peptide, antibody, interfering RNA, or small molecule. In some cases, the immune modulator is a monoclonal antibody, or an Ig fusion protein.

Non limiting examples of epigenetic drugs include DNA methyltransferase inhibitors (DNMTi), histone deacetylase inhibitors (HDACi), Non limiting examples of drugs for targeted cancer therapy include APR-246, As discussed above, and as demonstrated in the accompanying Examples, the inventors have shown that BET inhibitors have the following effects on tumor cells: increased interferon-gamma signalling; increased antigen presentation; suppressed constitutive and interferon-gamma-induced HLA class II expression; suppressed constitutive and interferon-gamma-induced indoleamine 2,3-dioxygenase (IDO) production; and suppressed constitutive and interferon-gamma-induced PD-L1 expression. Accordingly, in a further aspect, the invention provides the use of a BET inhibitor to increase interferon-gamma signalling in one or more tumor cell; and/or increase antigen presentation in one or more tumor cell; suppress constitutive and interferon-gamma-induced HLA class II expression in one or more tumor cell; suppress constitutive and interferon-gamma-induced indoleamine 2,3-dioxygenase (IDO) production in one or more tumor cell; and/or suppress constitutive and interferon-gamma-induced PD-L1 expression in one or more tumor cell. It will be appreciated by those skilled in the art that causing those effects in tumor cells will be beneficial in the generation of new therapeutic methods, uses and compositions.

In a preferred embodiment, the invention provides the use of a BET inhibitor to increase the expression and presentation of tumor-specific neo-antigens in one or more tumor cell.

Additionally, and in line with the inventors' findings, the invention provides the use of a BET inhibitor to have one or more of the following effects on tumor cells: increase interferon-gamma signalling; increase antigen presentation; suppress constitutive and interferon-gamma-induced HLA class II expression; suppress constitutive and interferon-gamma-induced indoleamine 2,3-dioxygenase (IDO) production; and suppress constitutive and interferon-gamma-induced PD-L1 expression. It will be appreciated by those skilled in the art that such uses will be beneficial in the generation of new therapeutic methods, uses and compositions.

The inventors surprising findings of the beneficial effects of BET inhibitors identifies new uses of such inhibitors, and identifies new sub-groups of patients with cancer that could be treated using BET inhibitors. As discussed above, BET inhibitors were previously described for use as an anti-tumor therapy for inhibiting tumor growth. However, the inventors' findings now demonstrate that BET inhibitors can be used to treat cancer in another way—specifically, by inducing and/or increasing antigen presentation of tumor cells, a tumor-specific T-cell response is induced in the patient, which leads to a tumor-specific immune response.

The inventors' findings identify several new sub-groups of patients with cancer that could be treated using BET inhibitors, in particular:

(i) patients with cancer which comprises tumor cells having no or low levels of expression and presentation of tumor-specific neo-antigens and/or shared antigens—in such patients, BETi enhances (interferon-gamma induced) presentation of antigens, leading to better recognition and eradication of the tumor by T cells; and/or (ii) patients with cancer which comprises HLA-negative tumor cells and/or PDL-1-negative tumor cells—in such patients, BETi enhances (interferon-gamma induced) expression of HLA, leading to better recognition and eradication of the tumor by T cells; and/or (iii) patients with cancer which comprises tumor cells having low or absent HLA class I expression—in such patients, BETi enhances (interferon-gamma induced) expression of HLA, leading to better recognition and eradication of the tumor by T cells; and/or (iv) patients with cancer which comprises tumor cells having poor interferon-gamma responsiveness and signalling—in such patients, BETi increases responsiveness of the tumors to interferon-gamma induced, leading to better antigen presentation and subsequently to better recognition and eradication of the tumor by T cells; and/or (v) patients with cancer with comprises tumor cells with high indoleamine 2,3-dioxygenase (IDO) expression (Holmgaard et al., 2015; Hornyák et al., 2018; Munn & Mellor, 2013)—in such patients, BETi suppresses (interferon-gamma induced) expression of IDO, leading to reduced immunosuppression of T cells, and thus better T cell-mediated eradication of the tumor; and/or (vi) patients with cancer which comprises tumor cells having high HLA class II expression (Donia et al., 2015; Hemon et al., 2011)—in such patients, BETi suppresses (interferon-gamma induced) expression of HLA class II. As will be appreciated, in healthy conditions, HLA class II is only expressed on professional antigen-presenting cells of the immune system (e.g dendritic cells), to promote immune responses—however, in pathological conditions, HLA class II is often aberrantly expressed on tumors, and serves to suppress immune responses in several ways, most importantly by being a ligand for LAG3, a molecule that, just like PD1, negatively regulates T cells and, in the case of CD4 T cells, skews them towards a suppressive phenotype; and/or (vii) patients with cancer which comprises tumor cells having elevated and/or high CD73 expression, for example compared to the normal level of expression of CD73 in a healthy cell (D. Allard, Chrobak, Allard, Messaoudi, & Stagg, 2018)—in such patients, BETi suppresses (interferon-gamma induced) expression of CD73, leading to reduced immunosuppression of T cells, and thus better T cell-mediated eradication of the tumor. CD73 catabolize the breakdown of extracellular ATP into adenosine, which suppresses T cells functioning.

Methods for identifying and characterising such tumor cells and the relevant molecular markers, and thereby identifying the patient sub-groups to be tested, are known to those skilled in the arts of medicine and molecular biology.

In a preferred aspect of the invention, there is provided a BET inhibitor for use in the treatment of cancer in a subject, wherein the treatment comprises administering of the composition to the subject, preferably wherein said administering comprises intradermal, subcutaneous, intramuscular, intravenous, or intratumoral administration or a combination thereof; and characterised in that the cancer in the subject comprises tumor cells that exhibit no or low levels of expression and presentation of tumor-specific neo-antigens.

In another preferred aspect of the invention, there is provided the use of a BET inhibitor in the manufacture of a medicament for the treatment of cancer in a subject, wherein the treatment comprises administering of the composition to the subject, preferably wherein said administering comprises intradermal, subcutaneous, intramuscular, intravenous, or intratumoral administration or a combination thereof; and characterised in that the cancer in the subject comprises tumor cells that exhibit no or low levels of expression and presentation of tumor-specific neo-antigens.

In another preferred aspect of the invention, there is provided a method for the treatment of cancer in a subject, the method comprising the step of administering to the subject a BET inhibitor, characterised in that the cancer in the subject comprises tumor cells that exhibit no or low levels of expression and presentation of tumor-specific neo-antigens.

Appropriate administration approaches, dosages, and regimens of BET inhibitors are known to those skilled in the art. Preferably, a BET inhibitor may be administered orally and/or by subcutaneous injection. Preferred dosages of a BET inhibitor are 1 mg per day, or 2 mg per day, or 5 mg per day, or 10 mg per day, or 20 mg/per day, or 30 mg per day, or 40 mg per day, or 50 mg per day, or 60 mg per day, or 70 mg per day, or 80 mg per day, or 90 mg per day, or 100 mg per day, or 150 mg per day, or 200 mg per day, or more. Preferably a BET inhibitor is administered in such dosages and/or by such routes once daily for 1 day or more, such as for 2, 3, 4, 5, 6, 7, 8, 9, 10, 11, 12, 13, 14, 21 or 28 days.

For example, the BET inhibitor R06870810 (a BET inhibitor based on JQ1) may be administered once daily (at escalating doses) via subcutaneous injection in either 28-day cycles (continuous 28 days dosing or 21 days dosing followed by 7 days off drug) or in 21-day cycle (14 days dosing followed by 7 days off drug).

The BET inhibitor OTX015/MK-8628 (a BET inhibitor) may be administered at a starting dose of 10 mg, orally (PO) once per day (QD) continuously for 21 days per cycle.

The BET inhibitor ZEN003694 may be administered orally once daily in 28-day cycles.

The BET inhibitor GSK525762 may be administered in a 5 milligram (mg) starting dose, orally, once per day. Dose escalations and/or dose adjustments may be performed to address tolerability and safety issues. Dose escalation may continue up to a dose of 200 mg per day is reached. GSK525762 may be provided in 1 mg, 10 mg and 30 mg tablets and/or administered with 240 milliliter (mL) water.

In a preferred aspect of the invention, there is provided a BET inhibitor for use in the treatment of cancer in a subject, wherein the treatment comprises administering of the composition to the subject, preferably wherein said administering comprises intradermal, subcutaneous, intramuscular, intravenous, or intratumoral administration or a combination thereof; and characterised in that the cancer in the subject comprises HLA-negative tumor cells and/or PDL-1-negative tumor cells.

In another preferred aspect of the invention, there is provided the use of a BET inhibitor in the manufacture of a medicament for the treatment of cancer in a subject, wherein the treatment comprises administering of the composition to the subject, preferably wherein said administering comprises intradermal, subcutaneous, intramuscular, intravenous, or intratumoral administration or a combination thereof; and characterised in that the cancer in the subject comprises HLA-negative tumor cells and/or PDL-1-negative tumor cells.

In another preferred aspect of the invention, there is provided a method for the treatment of cancer in a subject, the method comprising the step of administering to the subject a BET inhibitor, characterised in that the cancer in the subject comprises HLA-negative tumor cells and/or PDL-1-negative tumor cells.

Methods for identifying HLA-negative tumor cells and/or PD-L1-negative tumor cells are well known to those skilled in the arts of medicine and biochemistry.

Preferably in the methods and uses of the invention, administration of the BET inhibitor increases the expression and presentation of tumor-specific neo-antigens in the tumor cells of the cancer in the subject. Additionally, and in line with the inventors' findings, administration of the BET inhibitor increases interferon-gamma signalling; increases antigen presentation; suppresses constitutive and interferon-gamma-induced HLA class II expression; suppresses constitutive and interferon-gamma-induced indoleamine 2,3-dioxygenase (IDO) production; and suppresses constitutive and interferon-gamma-induced PD-L1 expression.

Preferably in the methods and uses of the invention, the BET inhibitor is combined with the systemic or localized administration of a drug selected from the group consisting of immunomodulatory compound, angiogenesis inhibitors, chemotherapeutics or c-Myc downregulation, preferably wherein the drug is an immunomodulatory compound selected from the group consisting: immunostimulatory cytokines, natural, endogenous or synthetic ligands of Toll like receptors, ligands of other immunostimulatory receptors, modulators of immune checkpoints, or agonistic modulators.

It will be appreciated that, where the BET inhibitor is administered in combination with such a drug, the BET inhibitor and the drug may be administered in any order—for example, the BET inhibitor may be administered before and/or concurrently with and/or after, the additional drug.

Furthermore, the BET inhibitor may be administered in combination with other anti-cancer therapies, including one or more of: radiation, surgery, chemotherapy, targeted therapy and/or checkpoint blockade therapy. It will be appreciated that, where the BET inhibitor is administered in combination with such a therapy, the BET inhibitor and the drug may be administered in any order—for example, the BET inhibitor may be administered before and/or concurrently with and/or after, the additional therapy.

In conclusion, this study for the first time demonstrates that BET inhibition can boost functional and antigen-specific T-cell responses against human melanoma cells, in a highly physiologically relevant model. Overall, the presented data indicate that JQ1, either alone or in combination with IFNγ, is able to strongly sensitize tumor cells for TIL recognition, irrespective of PD-L1 suppression. Importantly, we present evidence that BET inhibition induces its sensitizing effects primarily by potentiating the ability of IFNγ to activate APM components, independent from regulation of PD-L1. What's more, the fact that no sensitization is observed in KADA cells despite strong PD-L1 downregulation suggests that the sensitizing effects of JQ1 are primarily mediated by activation of the antigen-presentation machinery. In fact, we present evidence that BET inhibition can boost recognition of both tumor-associated antigens and tumor-specific mutant antigens, the latter of which have been proven particularly relevant for efficacy of anti-tumor T-cell responses during cancer immunotherapies.

It has been postulated before that immunosuppressive pathways are driven by the immune system rather than by cancer cells. For example, it was shown that induction of PD-L1, IDO and Tregs in the melanoma microenvironment is driven by CD8+ T cells 22. As this is primarily mediated through IFNγ production by CD8 T cells, the application of BET inhibitors might be a highly attractive way to enhance the positive effects of CD8 T-cells responses, while reducing the negative ones. This also suggests that cancer immunotherapy approaches targeting negative regulatory immune checkpoints might be more beneficial for patients with so-called 'hot' tumors (i.e. having pre-existing T-cell infiltrations). On the other hand, the method according to the invention is especially suited for the treatment of patients having so-called 'cold' tumors (i.e. having no T-cell infiltrations), as it triggers an influx of T cells through activation of the APM.

A very recent study in Nature, based on a CRISPR-Cas9 library to mimic loss-of-function mutations in melanoma, found that the majority of genes involved in resistance to T-cell based cancer immunotherapies have key roles in antigen presentation and IFNγ signaling, and correlate with cytolytic activity in patient tumors from The Cancer Genome Atlas.23 The fact that our findings show that BETi affect precisely these pathways gives further support to the notion that they could be highly instrumental for improving the clinical efficacy of T-cell based immunotherapies. At the same time, BETi display clear anti-proliferative capacities in cell cultures, making them a highly attractive type of anti-cancer medicine that affects tumors at multiple levels.

Summarizing: Inhibitors of Bromodomain and extra-terminal domain (BET) family members, are known to induce multiple effects in tumors. Whilst originally intended for use as targeted therapy to suppress proliferation and induce apoptosis, BET inhibition was recently found to strongly suppress expression of PD-L1 in various tumor mouse models and human cancer cell lines. Although this was also shown in human melanoma cells, it has never been studied what functional consequences this has for anti-tumor immune responses. Therefore, we set out to determine the importance of these mechanisms for functional immunogenicity of human melanoma cells.

Early-passage human melanoma cell lines were treated for 72 hours with the BET inhibitor JQ1, either alone or in combination with interferon-gamma (IFNγ). Cells were subsequently trypsinized, washed and co-cultured for 24 hours with autologous tumor-infiltrating lymphocytes (TIL). Co-culture supernatants were assessed by ELISA for IFNγ levels, as a measure for tumor recognition by the TIL. Cell lines were also assessed by flow cytometry for expression levels of PD-L1 after treatment with JQ1 and/or IFNγ.

Treatment of early-passage tumor cell lines with JQ1, either alone or in combination IFNγ, markedly sensitized them for recognition by autologous TIL. Importantly, JQ1 clearly enhanced the ability of IFNγ to induce HLA class I, (32 microglobulin, and components of the antigen-presentation machinery. Although PD-L1 expression was indeed suppressed by JQ1, its enhancing effect on IFNγ-induced antigen-presentation coincided much more strongly with improved functional recognition by TIL. This was also emphasized by the observation that sensitizing effect of JQ1 was even observed when cells were negative for PD-L1 at baseline and after IFNγ treatment. We conclude that BET inhibition is indeed able to promote anti-tumor immunity against human melanoma cells, possibly also through mechanisms independent from PD-L1 suppression.

EXAMPLES

Example 1: Materials and Methods

Cell Lines and Culture

The early-passage melanoma cell lines ANRU, ROAL and KADA were established from patients at the oncology clinic at Karolinska University Hospital (ethical permit: #2011/143-32/1) based on a published protocol.21 Mycoplasma-free (MycoAlert kit) cell lines were in their 15th to 45th passage when used in this study.

Culture and Expansion of Tumor-Infiltrating Lymphocytes

Culture and expansion of tumor-infiltrating lymphocytes was done as published before.[4] A piece of the tumor (approximately 0.5 cm3) was minced into 1 mm3 pieces. Each piece was placed in one well of a 24-well plate containing 1 mL/well CellGro medium supplemented with 2% autologous plasma (generated by centrifugation and heat-inactivation of plasma collected on the day of surgery) and 6,000 IU/mL IL-2 (Proleukin, Novartis, Basel, Switzerland). On day 1 of culture, half of the medium volume in each well was replaced with fresh medium supplemented with plasma and IL-2. After 3-4 days of culture, lymphocytes could usually be seen emerging from the tumor piece. Cultures were monitored regularly and split before reaching confluence. After approximately 2 weeks, expanding wells were pooled and counted. To generate large T cell numbers, TIL were cultured for approximately 14 days in presence of autologous, irradiated feeders (40 Gy, TIL:feeder ratio 1:50-1:80) with 300 IU/mL IL-2 and 30 ng/mL anti-CD3 antibody (OKT3, Cilag, Zug, Switzerland). Cells were split or medium exchanged as necessary. Cultures were initiated in standing T75 flasks, but transferred to VueLife cell culture bags 1 week before harvest. At the end of culture, cells were harvested, pooled, characterized, counted and frozen.

Flow Cytometry

Flow cytometry was done after staining with the following antibodies: anti-human HLA-ABC APC-Cy7 (clone W6/32; Biolegend, San Diego, CA, USA), CD274 BV786 (clone MIH1; BD Biosciences, Franklin lakes, NJ, USA). All data were acquired on a Novocyte 2000 [?] flow cytometer (Acea Biosciences, San Diego, CA, USA) were analyzed using FlowJo software version 10 (Treestar).

Example 2: JQ1 Differentially Sensitizes Melanoma Cells for Recognition by Autologous TIL We show herein that treating patient-derived early-passage melanoma cell lines with JQ1 enhances recognition by autologous TIL. To study potential suppressive effects of BET inhibition on both constitutive and induced PD-L1 expression, we also studied the sensitizing effect of JQ1 in combination with IFNγ. In addition, cells were treated by IFNγ alone to get an idea of the strength of potential sensitizing effects of JQ1 compared to a known physiological cue for sensitization of target cells for T-cell recognition. Along with this, PD-L1 and HLA class I expression were assessed by flow cytometry in pretreated tumor cells to find out whether functional observations in the tumor-TIL co-cultures would be associated with changes in PD-L1 expression or HLA class I expression, both markers being key determinants of T-cell activation upon target cell recognition.

After culture of ANRU for 72 hours in the presence of JQ1 alone and subsequent co-culture for 24 hours with autologous TIL, we observed a dose-dependent increase in T-cell recognition, as indicated by increased levels of IFNγ production (FIG. 1a, top row). In contrast, pretreatment of ANRU with IFNγ alone or in combination with JQ1 did not lead to any increases in T-cell recognition during co-culture (FIG. 1a, second row). Interestingly, these observations did not coincide with any effects on expression of PD-L1, as expression of this molecule on ANRU cells was wholly absent under all conditions. At the same time, we did observe a consistent enhancement of HLA class I induction by IFNγ in the presence of JQ1, while upregulation of HLA class II was actually suppressed (FIG. 1).

In contrast to our findings with ANRU, pretreatment with JQ1 alone did not sensitize the early-passage cell lines ROAL and KADA for recognition by autologous TIL, even at higher concentrations. In the case of ROAL, treatment with IFNγ alone did not sensitize the cells for recognition by autologous TIL. However, TIL did significantly better and synergistically recognize ROAL cells pretreated with a combination of JQ1 and IFNγ. Similar to what was observed for ANRU, PD-L1 expression on ROAL cells was marginal if not absent under all conditions, while HLA class I expression again was significantly more strongly induced by IFNγ in the presence of JQ1.

Results for KADA stood out in multiple ways from the others. Firstly, IFNγ pretreatment strongly sensitized KADA for recognition to TIL, while a combination of IFNγ and JQ1 in fact led to a reduction in tumor cell recognition by autologous TIL. Strikingly, KADA displayed high constitutive and even higher IFNγ-induced PD-L1 expression levels that were strongly suppressed by JQ1. Again in contrast to what was observed for ANRU and ROAL, JQ1 actually reduced HLA class I induction by IFNγ. Of note, tumor recognition by TIL after any pretreatment was always and fully abrogated when co-cultures were done in the presence of an HLA class I blocking antibody.

Together, these data indicate that JQ1, either alone or in combination with IFNγ, is able to markedly sensitize tumor cells for recognition by TIL, in the absence of PD-L1 expression. These effects were observed only in cell lines with enhanced induction of HLA class I by IFNγ in the presence of JQ1. In contrast, JQ1 failed to sensitize melanoma cells and even reduced IFNγ-induced sensitization despite strong PD-L1 suppression. The fact that no sensitization is observed in KADA cells despite strong PD-L1 downregulation suggests that the sensitizing effects of JQ1, and perhaps also the immunological effects observed in other studies, are primarily mediated by activation of the antigen-presentation machinery.

Example 3: JQ1 Enhances Tumor Recognition by TIL Independently from PD-L1

Next, we set out to further confirm that JQ1 can enhance functional tumor recognition by TIL regardless of any effect on PD-L1. To test this, we co-cultured ANRU tumor cells for 24 hours with autologous TIL in the presence and absence of a PD-L1 blocking antibody. Suitable PD-L1 blocking antibodies are commercially available, and include anti-human CD274 (B7-H1, PD-L1) Antibody (clone 29E.2A3; Cat No. 329709; Biolegend), anti-human CD274 (B7-H1, PD-L1) Antibody (clone MIH3; Cat No. 374502; Biolegend), Anti-PD-L1 (CD274) Neutralizing Antibody (Cat No. 71213; BPS Bioscience), PD-L1/B7-H1/CD274 Blocking Antibody (clone R639; Cat No. 10084-R639; Sino Biological) and Human PD-L1/B7-H1 Antibody (Cat No. AF156; R and D Systems). Tumors cell were pretreated for 12, 24, 48 and 72 hours, to check for any PD-L1 induction or suppression over time by flow cytometry, and to define the time kinetics of JQ1-induced sensitization of tumors for recognition by TIL in a co-culture. We reasoned that recognition by autologous TIL should not be affected by PD-L1 blockade at any time point if ANRU tumor cells would be PD-L1 negative under all conditions. Indeed, no effect of PD-L1 blockade was seen in the ANRU tumor-TIL co-culture after any of the pretreatments (FIG. 2). In addition, IFNγ pretreatment for any time duration did not lead to an improvement of tumor recognition by the TIL. Improved recognition by TIL was only observed in case tumors were incubated with JQ1, while the effects were clearly most prominent after pretreatment with JQ1 alone for 72 hours.

Example 4: JQ1 Potentiates IFNγ-Induced Activation of the Antigen-Presentation Machinery The data in FIG. 1 demonstrate that JQ1 enhances HLA class I induction by IFNγ on ANRU and ROAL and A375 cells. Moreover, the presence of a HLA class I blocking antibody always fully abrogated T-cell recognition in co-cultures with pretreated tumors. This led us to hypothesize that JQ1 induces its effects at the level of antigen-presentation in these cell lines. Therefore, we studied mRNA and protein expression of well-known components of the antigen-presentation machinery (APM) after pretreatment with JQ1 alone and/or IFNγ. We found that JQ1 for nearly of these components potentiated their induction by IFNγ (FIG. 3a), the most pronounced effects being observed for HLA class I, beta-2 microglobulin (B2M), TAP1 and TAP2.

To study the time kinetics of these effects, the ANRU cell line was treated in the same way for 12, 24, 48 and 72 hours. Again JQ1 potentiated the induction of APM components by IFNγ at all time points (FIG. 3b). Enhanced induction of APM components by IFNγ in the presence of JQ1 could also be seen at the protein level, as illustrated by western blot for TAP1, TAP2, Tapasin, HLA class I heavy chain, LMP2 and LMP10 (FIG. 3c). This was most apparent for HLA class I heavy chain, and overall was most clearly seen in A375 cells.

Example 5: JQ1 Enhances Recognition of Tumor-Associated and Mutant Antigens by Autologous TIL Herein, we addressed the question whether enhanced tumor recognition by autologous TIL after JQ1 treatment is directed at tumor-associated antigens or tumor-specific mutant antigens. Therefore we co-cultured ANRU cells with TIL sorted for their specifity towards either the tumor-associated antigen MART-1, or two different tumor-specific mutant antigens, designated ETV6.9 and NUP210. We found that JQ1 improved recognition by all three TIL populations, too a similar or much stronger extent as compared to IFNγ alone (FIG. 4). This suggests that BET inhibition can indeed improve recognition of various types of tumor-antigens.

Example 6: JQ1 Dose-Dependently Enhances Induction of HLA Class I by IFNγ

To further confirm the ability of JQ1 to potentiate HLA class I induction on human melanoma cells, we tested the effect of increasing JQ1 concentrations in combination with a standard concentration of IFNγ. Both on A375 and ROAL cells we detected a clear dose-dependent enhancement of HLA class I induction by IFNγ in the presence of JQ1 (FIG. 5, top row). Similar observations were made for ANRU cells (data not shown).

Example 7: Dose-Dependent Enhancement of HLA Class I Induction by IFNγ in the Presence of I-BET151 and I-BET762

To assess whether other BETi would be able to mediate similar effects on HLA class I as JQ1, we treated A375 and ROAL cells with I-BET151 and I-BET762 alone or in combination with IFNγ. We found that HLA class I induction by IFNγ was clearly increased when used in combination with these BETi (FIG. 5, second and third row). This suggests that the ability to boost HLA class I expression, especially in combination with IFNγ, is a universal feature of BETi.

Example 8: Basic Protocol for Treatment of Autologous Tumor Cells with Small-Molecular BET Inhibitors or any Other Means of BET Inhibition For each patient an autologous tumor cell line was established as described herein.
Tumor cells were treated for at least 1 day with a BET inhibitor (BETi). During or after BETi treatment, tumor cells may be also exposed to interferon-gamma (IFNγ) and/or a variety of other immunostimulatory compounds (e.g. type I interferons).
Effects of BETi on tumor cell immunogenicity were evaluated by determining expression changes in a variety of immunological markers, including HLA class I and II, PD-L1 and Indoleamine 2,3-dioxygenase, and their ability to activate autologous tumor-infiltrating lymphocytes (TIL) in a co-culture.

Example 9: Potential Uses of BETi-Treated Tumors, Applied Either Alone or in Combination with Each Other 1. Use as a personalised therapeutic cancer vaccine, by administrating to a patient autologous BETi-treated tumors cells that have been irradiated or subjected to any other method to prevent them from being tumorigenic in vivo.
2. To promote ex vivo activation and expansion of tumor-antigen-specific TIL (such as autologous tumour-antigen-specific TIL) or autologous PBMC that can be used for adoptive cell therapies, for example according to protocol 2 (see below)(Dijkstra et al., 2018).
3. To promote presentation of tumor-specific antigens by (professional) antigen-presenting cells (APC) ex vivo for use in adoptive cell therapies, for example according to protocol 2 (see below).
4. To identify tumor-specific antigens, for example according to protocol X (see below)
5. To validate presentation and immunogenicity of epitopes predicted by bioinformatics tools.

Example 10: Use as a Personalised Therapeutic Vaccine

Important parameters regarding administration to the patient:
Numbers of tumor cells injected may range from 10 to $1 \times 10^{13}$
Tumor cells can be injected intradermally (i.d.), subcutaneously (s.c.), intramuscularly (i.m.) or intravenously (i.v.) and intratumorally (i.t).
Injections may be done once or can be repeated for any number of times, with any kind of frequency (e.g. daily, weekly, monthly, yearly).
All patients receiving ex vivo treated autologous tumors cells may be pretreated, or concurrently or subsequently treated in any way (e.g. by irradiation, chemotherapy, targeted compounds and immunomodulators, or combinations thereof) can be expected to produce the best result of treatment with the BETi-treated tumor cells.

Example 11: Use of BETi-Treated Autologous Tumor Cells to Promote Ex Vivo Activation and Expansion of Tumor-Antigen-Specific TIL For each patient an autologous tumor cell line was established as described herein.
Tumor cells were treated for 72 hours or longer with either BETi. During or after BETi treatment, tumor cells may be also exposed to interferon-gamma (IFNγ) and/or a variety of other immunostimulatory compounds (e.g. type I interferons).
Either subsequently or simultaneously, tumor cells are co-cultured with autologous tumor-infiltrating lymphocytes or T cells from autologous PBMC generated as described herein.
During co-culture, additional immunostimulatory compounds may be added, such as interleukin-2 and the agonistic anti-human CD3ε antibody OKT3.
Low concentrations of BETi may also be present during TIL expansion or expansion of T cells from autologous PBMC, as this has been shown to enhance T cell persistence and function in adoptive immunotherapy models[24].

Example 12: Use of BETi-Treated Autologous Tumor Cells to Enhance Antigen-Presentation by Professional Antigen-Presenting Cells (APC)

Autologous primary dendritic cells, monocyte-derived dendritic cells, or artificial APC can be exposed ex vivo to whole or fragmented BETi-treated autologous tumors.

Example 13: Use of BETi-Treated Autologous Tumor Cells to Identify Immunogenic Tumor-Specific Antigens Co-culture of BETi-treated tumors with autologous TIL and/or peripheral T cells.
Determine and sort T-cell clones most strongly activated in this co-culture Assess the antigen-specificity of the identified T-cell clones Use information to design personalised peptide-, RNA- or DNA-based vaccines that can be administered to patients after or concurrent with treatment with immunostimulatory compounds, including BETi.

BETi-treated autologous tumor cells may also be used to validate presentation and immunogenicity of tumor-specific antigenic epitopes predicted by bioinformatics tools using DNA sequencing data (e.g. whole-exome sequencinf data).

Example 14: Protocols

Protocol 1A: Generation of Tumor Cell Lines

Early-passage melanoma cell lines are generated according to a published protocol.[25] In brief, cell lines are established by the following steps:
1) From the primary tumor and/or a distant metastasis, a tumor tissue specimen is obtained by surgical resection, fine-needle aspiration or other means, and kept in complete RPMI-1640 medium with 15% fetal bovine serum (from here on referred to as R15) for transport.
2) Cells released from the tissue into the medium during transport are collected and placed separately into culture in R15.
3) The tumor tissue specimen is weighed and minced with scalpels in R15.
4) Cells released during mincing are placed separately into culture in R15.
5) Remaining tissue chunks are digested with 3125 Units/g collagenase type 1 in RPMI+5% FBS in a spinner flask at 37° C. and 5% $CO_2$ for 1-4 h depending on tissue types. For a fibrotic tumor tissue, 6250 Units/g collagenase type 1 can be used.
6) After digestion, cells are washed twice and cryopreserved or directly cultured in tissue culture flasks with R15.
7) Differential attachment, nutritional starvation and differential trypsinization procedures are used to eliminate fibroblast contamination.
8) Isolated tumor cells are grown in R15 in tissue culture flasks, changing medium twice weekly or more often if necessary, until a confluent monolayer is established. At the time of confluence, adherent cells are washed once with room-temperature calcium and magnesium-free phosphate buffered saline (PBS) and detached using trypsin/EDTA and resuspended in R15 medium.
9) Cultured tumor cells are routinely trypsinized, harvested, and suspended at 10-20 $10^6$ cells/ml in cold cryopreservation medium in cryovials.

Protocol 1B: Example of a Basic Protocol for Treatment of Autologous Tumor Cells with Small-Molecular BET Inhibitors (BETi) or any Other Means of BET Inhibition.
1) For each patient an autologous tumor cell line is established according to protocol 1A.
2) Tumor cells are treated for at least 1 day by any means to inhibited BET proteins, for example JQ1 at a concentration between 0.1 and 10 μM.
3) Before, during or after BETi treatment, tumor cells may be also exposed to:
Interferon-gamma (IFNγ)
Any other immunostimulatory compounds (e.g. type I interferons)
Any targeted compound with cancer selectivity (e.g. BRAF and MEK inhibitors).
4) Effects of BETi on tumor cell immunogenicity will be evaluated by:
Determining expression changes in a variety of immunological markers, including HLA class I and II, PD-L1 and Indoleamine 2,3-dioxygenase.
Their ability to activate autologous tumor-infiltrating lymphocytes (TIL) in a co-culture.

Optional Modifications

Tumors (cells) used in step 4 may be treated by any means to inhibited BET proteins, for example JQ1 at a concentration between 0.1 and 100 μM. Treatment may also be done in combination with IFNγ at a concentration between 1 and 10000 ng/ml, or any other immunostimulatory compounds (e.g. type I interferons), or targeted compound that can be expected to improve treatment of patient with BETi-treated cells.

Treatment of tumor cells may take place before co-culture with iDC, for a duration of 1 to 30 days, or longer. Alternatively, treatment of tumor cells may take place during co-culture with iDC, as both BET bromodomain inhibition and IFNγ have been described to promote immunogenicity of DC.

Tumor cells may also undergo transduction with genes encoding co-stimulatory molecules CD80, CD86, CD70 and/or immuno-stimulatory cytokines of the gamma C family, CD83 and dendritic cell or T-cell attracting chemokines, or any other molecule that can enhance the functioning of BET-treated tumors as antigen-presenting cells.

Protocol 2: Culture and Expansion of Tumor-Infiltrating Lymphocytes
1) A tumor biopsy (of approximately 0.5 cm3) is obtained from the primary tumor or a distant metastasis.
2) Tumor tissue is minced into 1 mm3 pieces.
3) Tumor piece are each placed in one well of a 24-well plate containing 1 mL/well CellGro medium supplemented with:
2% autologous plasma (generated on the day tissue is obtained)
6,000 IU/mL interleukin-2 (IL-2)
4) Day 1 of culture: half of the medium volume in each well is replaced with fresh medium supplemented with autologous plasma and IL-2.
5) Day 3-4 days of culture: lymphocytes usually start emerging
6) Cultures are monitored regularly and split before reaching confluence.
7) After approximately 2 weeks: wells with expanding cells are pooled and counted.
8) To generate large cell numbers, TIL are cultured for approximately 14 days in presence of:
Autologous, irradiated PBMC (40 Gy, TIL:feeder ratio 1:50-1:80)
300 IU/mL IL-2
30 ng/mL anti-CD3 antibody (OKT3)
9) Cells are split or medium exchanged as necessary.
10) Cultures are initiated in standing T75 flasks, but can be transferred to VueLife cell culture bags 1 week before harvest.
11) At the end, cells are harvested, pooled, characterized, counted and frozen.

Protocol 3: Generation of Mononcyte-Derived Dendritic Cells

Dendritic cells (DC) are generated according to a published protocol.[26] Briefly, the protocol includes the following steps:

1) Monocytes are isolated from leukapheresis products by elutriation
2) Monocytes are cultured in CellGro medium at 2 million cells/mL in VueLife cell culture bags in presence of:
   100 ng/mL granulocyte macrophage colony-stimulating factor (GM-CSF)
   20 ng/mL interleukin-4 (IL-4).
3) Day 2 of culture: one volume of fresh cytokine-containing medium is added.
4) Day 5 of culture:
   Immature DC (iDC) may be exposed to:
   i) Autologous tumor lysate (10-30 µg per million cells), for example derived from tumor cells that may have been exposed ex vivo to BETi
   ii) Autologous tumor cells (whole), for example that may have been exposed ex vivo to BETi.
   iii) Autologous tumor cells (for example which may have first been exposed ex vivo BETi), lysed or fragmented by any means
   Before addition, tumor cells may be irradiated, or treated in any other way, to prevent them from growing out in co-culture with DC.
   Cell numbers of iDC are adjusted to 2 million cells/mL in medium supplemented with IL-4 and GM-CSF as above.
   Maturation of iDC is induced by addition of:
   i) 20 ng/mL tumor necrosis factor (TNF)-α
   ii) Any (combination of) other immunostimulatory compounds that can mature iDC, e.g. ligands for Toll-like receptors, or interferon-gamma (IFNγ).
5) On day 7, mature DC (mDC) are harvested, counted, characterized and frozen in aliquots of 17.5 million cells. Extra steps may included here to wash away, or remove by any other means, compounds used for iDC maturation.
6) On the day(s) of DC vaccination, one ampule of frozen mDC is rapidly thawed in a 37° C. water bath, counted and the viability is assessed. Cells are resuspended in 0.2 mL NaCl (0.15 M) and administered intra-dermally using an insulin syringe.

Tumors (cells) used in step 4 may be treated by any means to inhibited BET proteins, for example JQ1 at a concentration between 0.1 and 10 µM. Treatment may also be done in combination with IFNγ at a concentration between 1 and 200 ng/ml. Treatment of tumor cells may take place before co-culture with iDC, for a duration of 1 to 5 days. Alternatively, treatment of tumor cells may take place during co-culture with iDC, as both BET bromodomain inhibition and IFNγ have been described to promote immunogenicity of DC.

Protocol 4: General Guidelines for Treatment of Patients with BETi-Treated Tumors
   All patients to which ex vivo treated autologous tumors cells are administered may be pretreated in any way (e.g. by irradiation, chemotherapy, targeted compounds, epigenetic drugs and immunomodulators, or combinations thereof) that is not severely immunosuppressive and can be expected to produce the best result of treatment with the BETi-treated tumor cells.
   Patients to which ex vivo BETi-treated autologous tumors cells are administered may be concurrently or subsequently treated in any way that can be expected to produce the best result of treatment with the BETi-treated tumor cells, in particular immunomodulatory agents that can be expected to further enhance the effect of treatment with BETi treated autologous tumor cells.
   These guidelines do not exclude the possibility of treating patients with ex vivo BETi-treated autologous tumors cells that underwent earlier, are having concurrent or will undergo future treatments that may actually not beneficially affect clinical outcome of treatment with ex vivo BETi-treated autologous tumors cells.

As shown in FIG. 6, JQ1 enhances IFNγ-induced HLA class I expression and suppression constitutive and IFNγ-induced of multiple immune checkpoint molecules.

As shown in FIG. 7, JQ1 potentiates IFNγ-induced activation of the antigen-presentation machinery and enhances expression of key proteins in the IFNγ-signaling pathway.

As shown in FIG. 8, JQ1 potentiates IFNγ-induced activation of the antigen-presentation machinery and enhances expression of key proteins in the IFNγ-signaling pathway.

Figure 1:
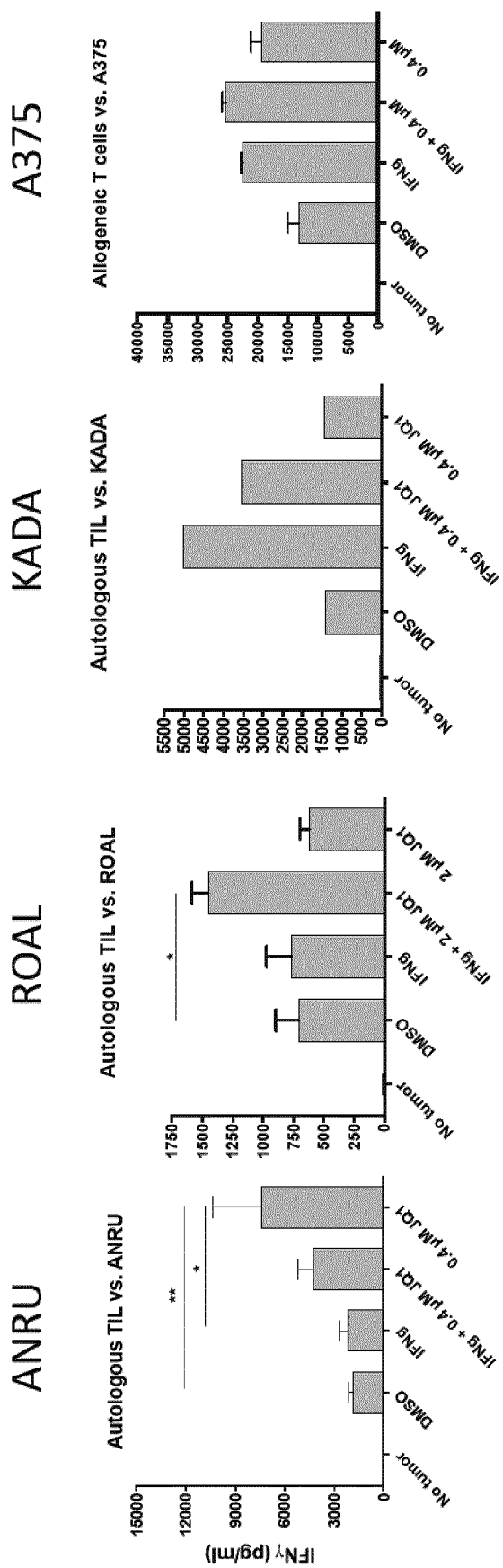
Figure 1:
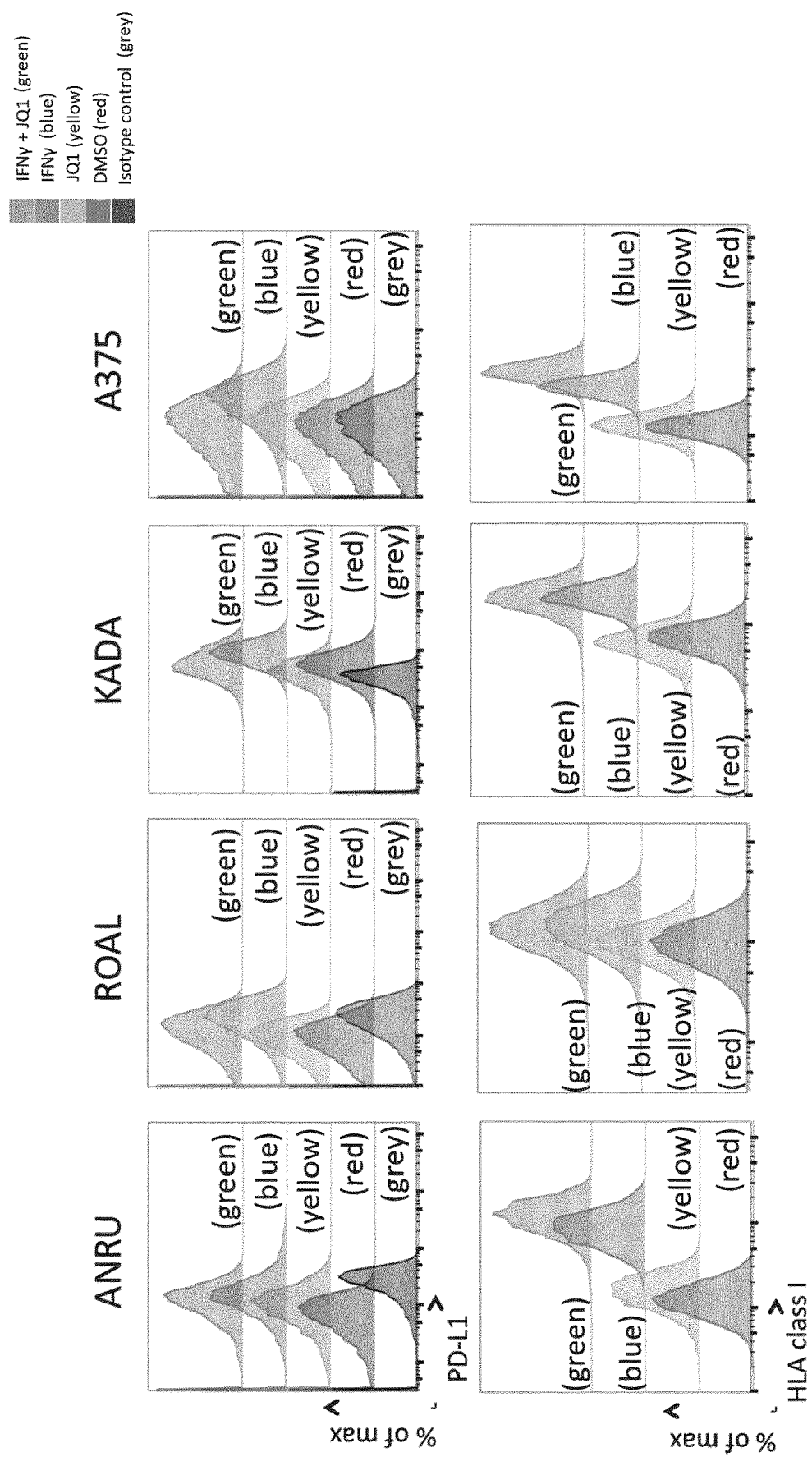
Figure 1:
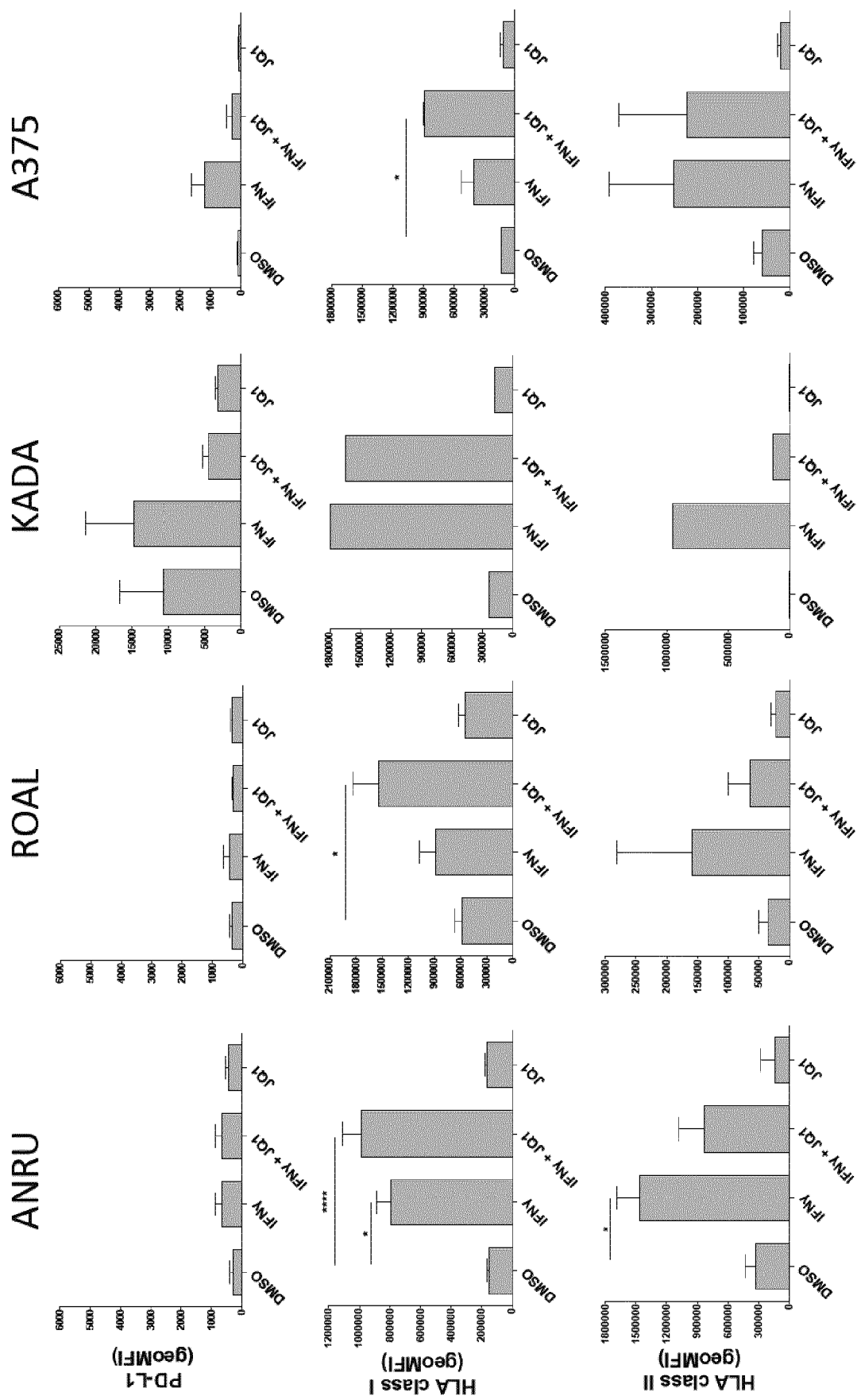
Figure 2:
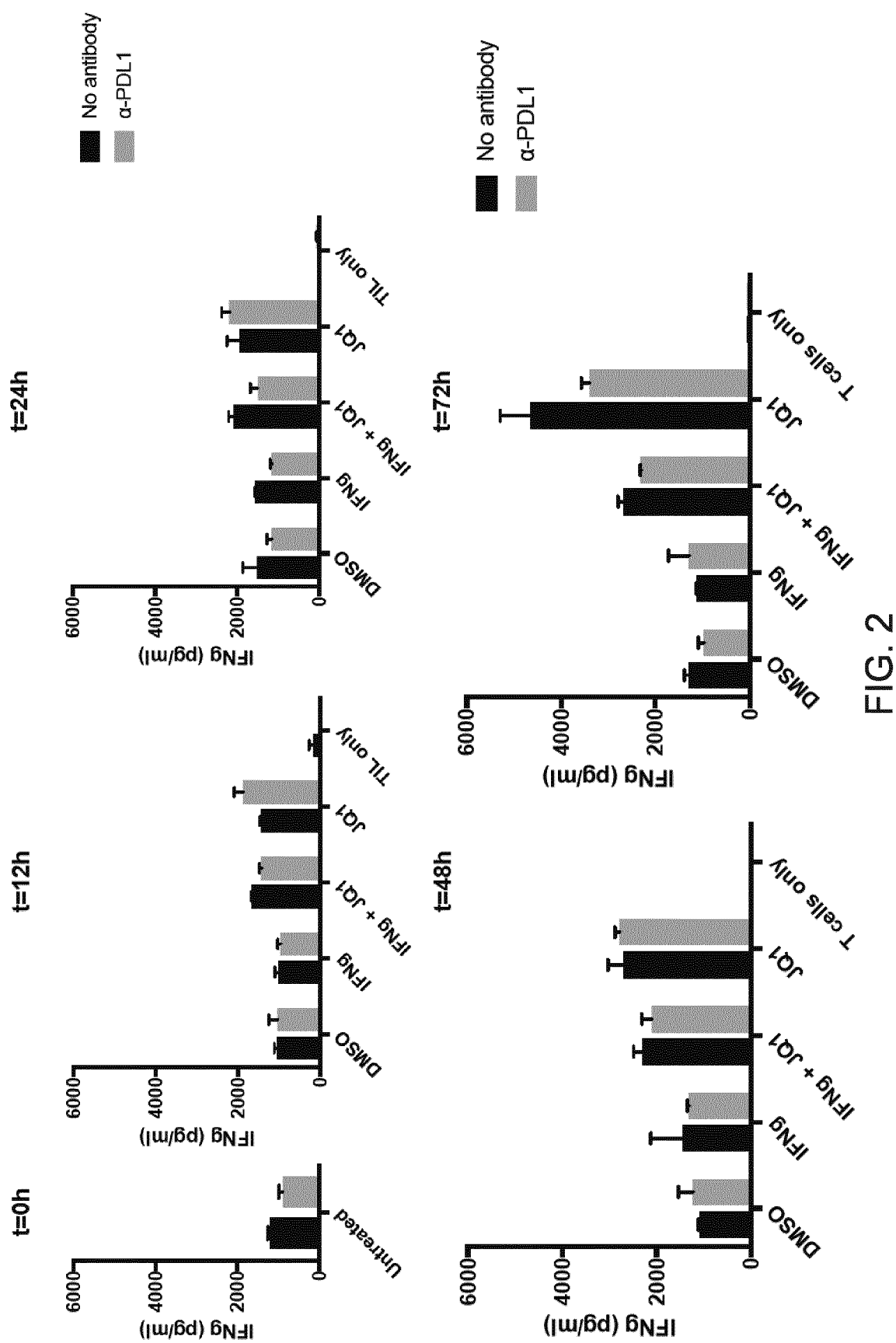
Figure 3A:
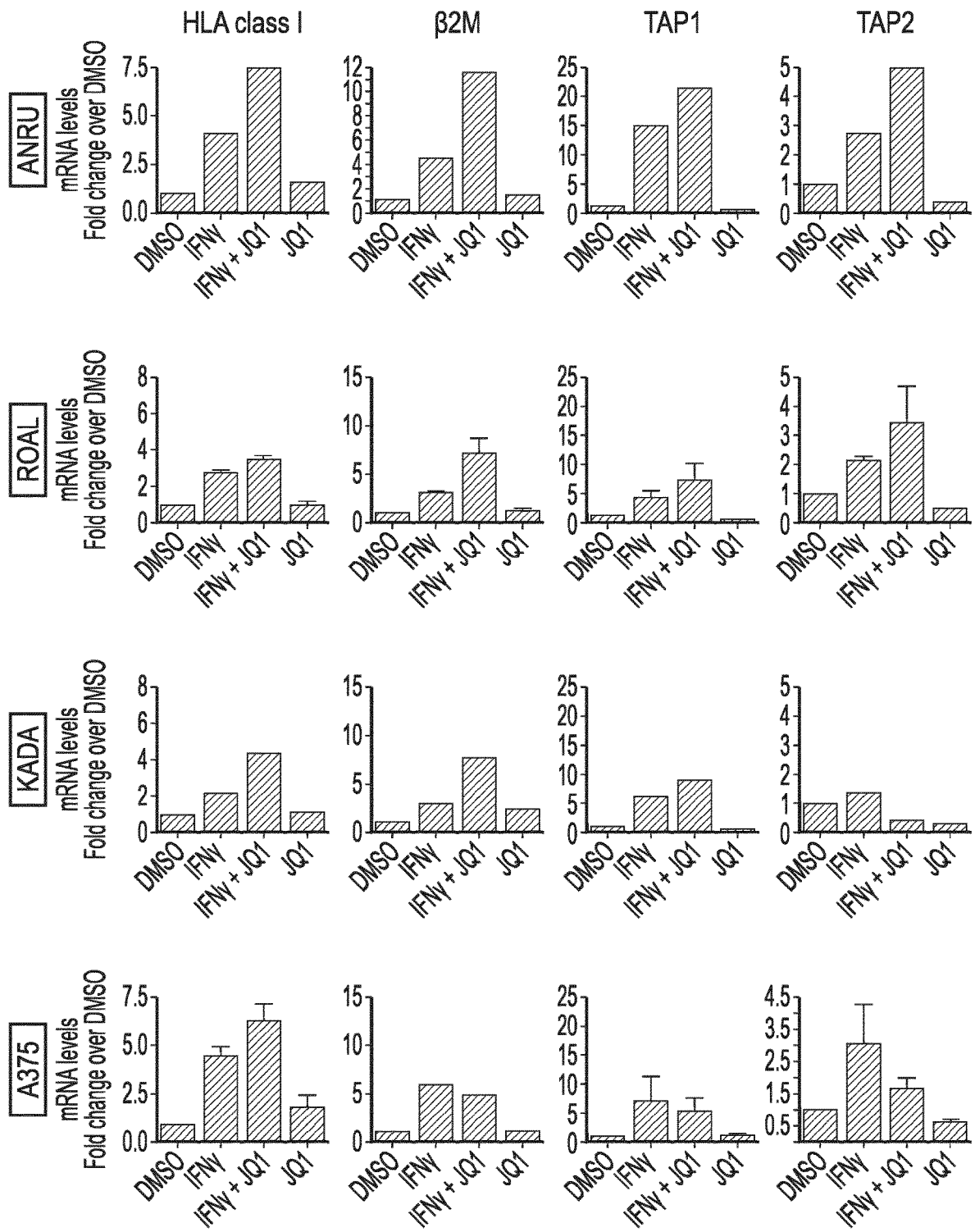
Figure 3A:
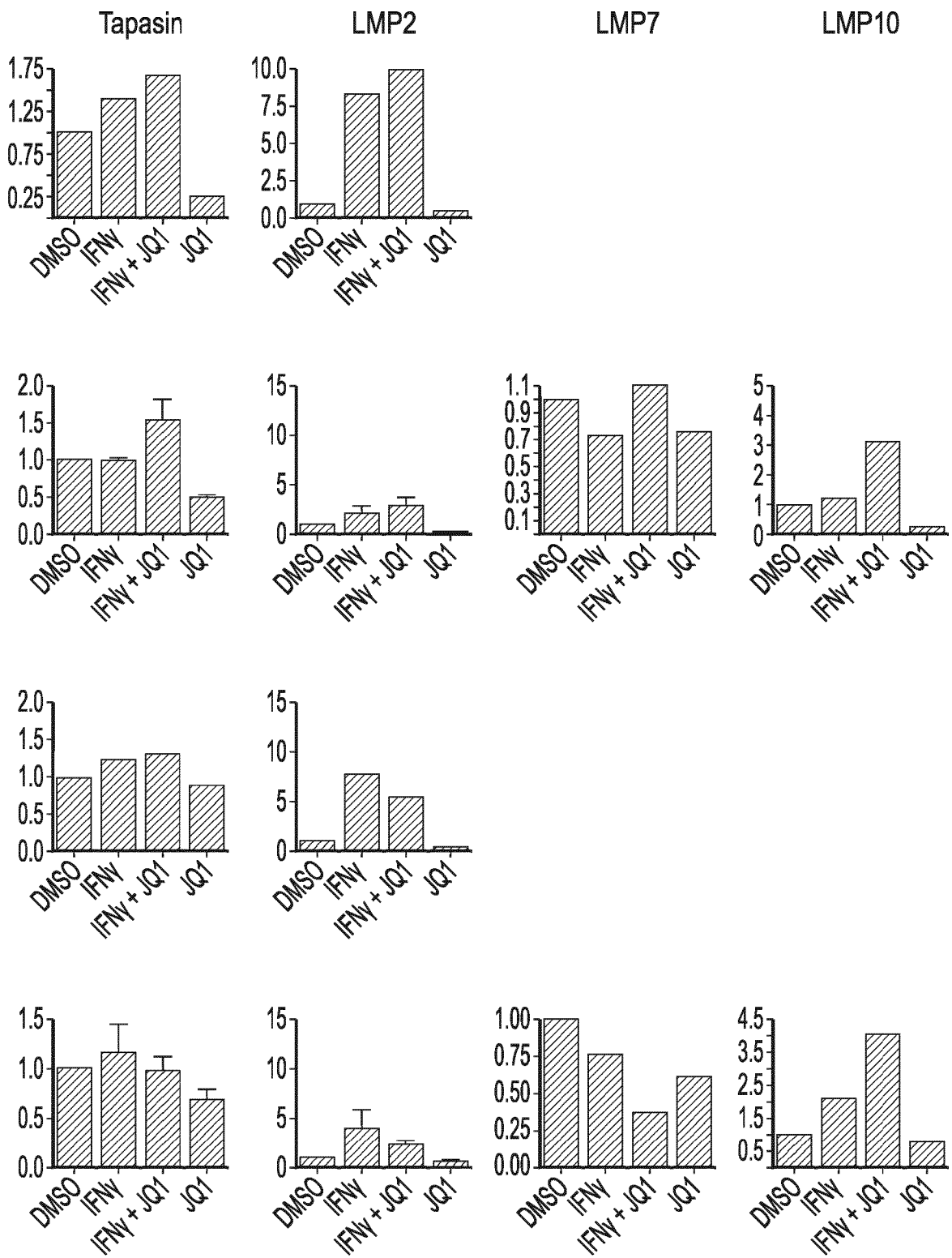
Figure 3B:
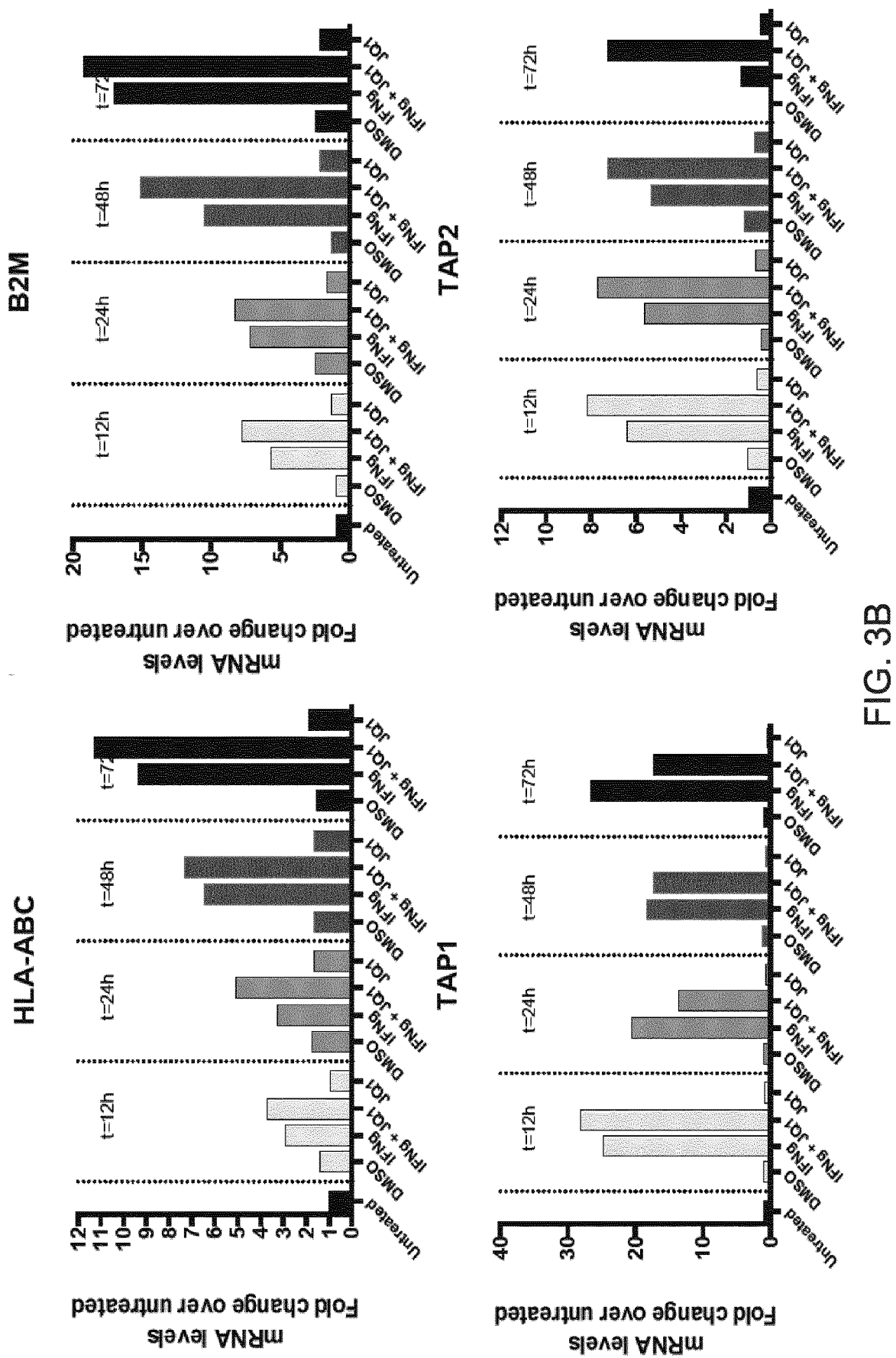
Figure 3B:
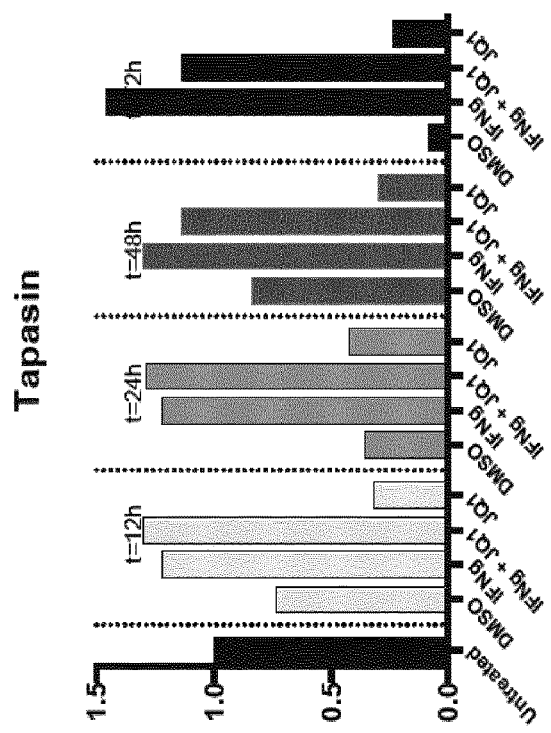
Figure 3B:
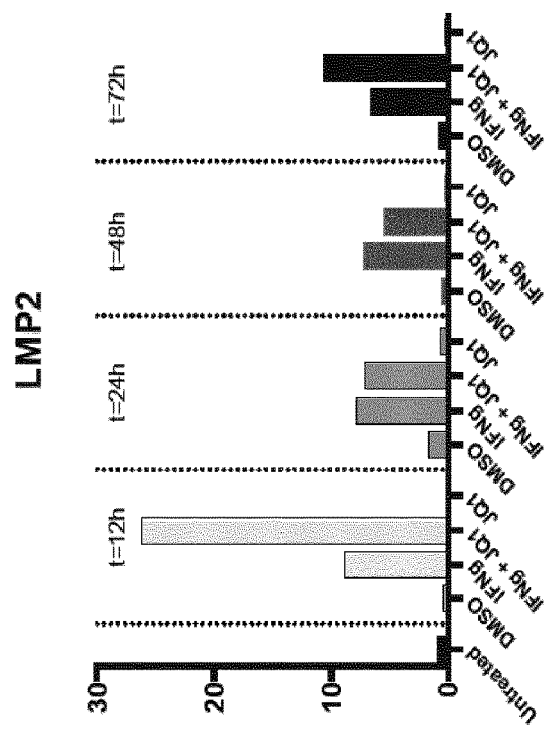
Figure 3C:
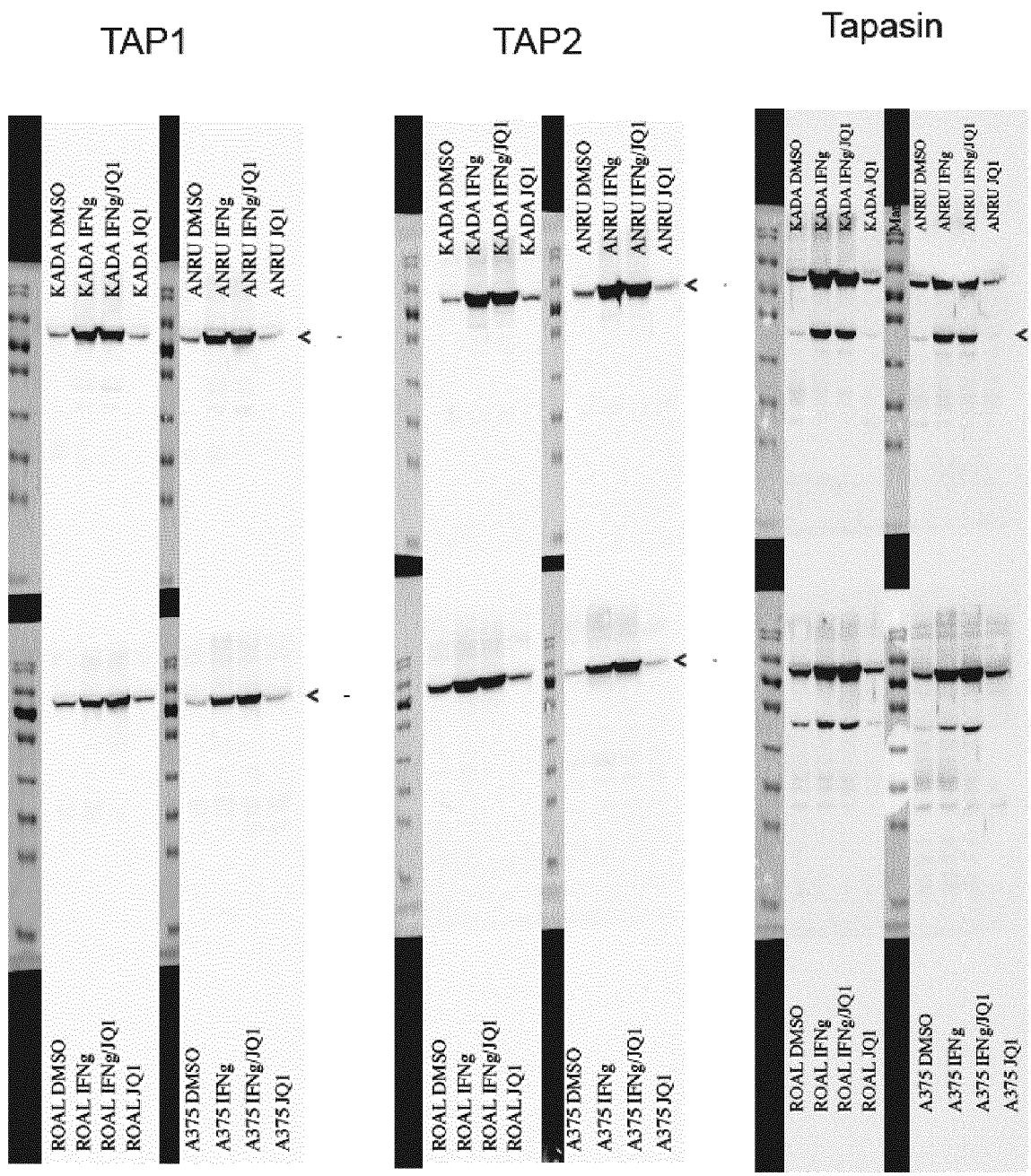
Figure 3C:
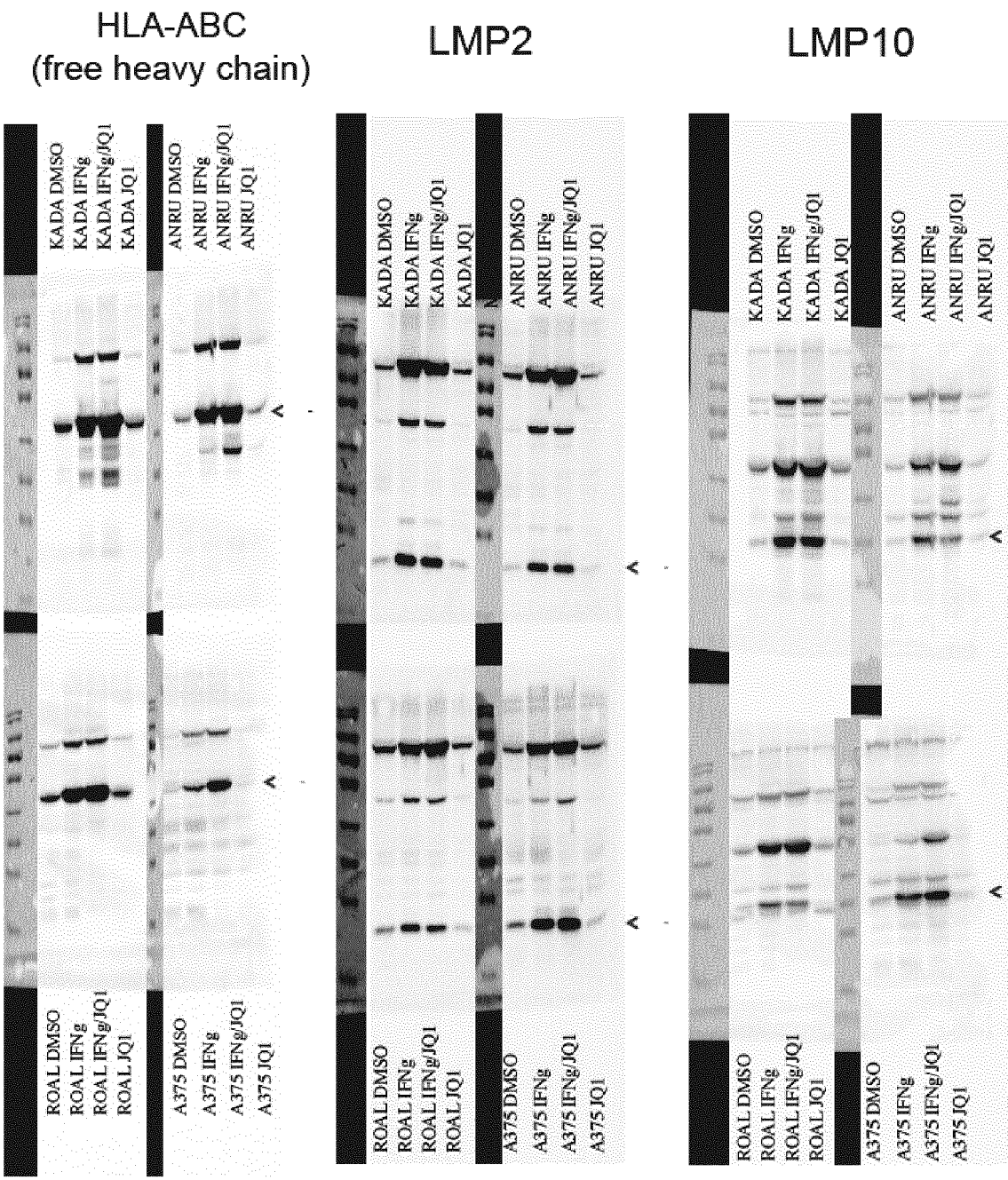
Figure 4:
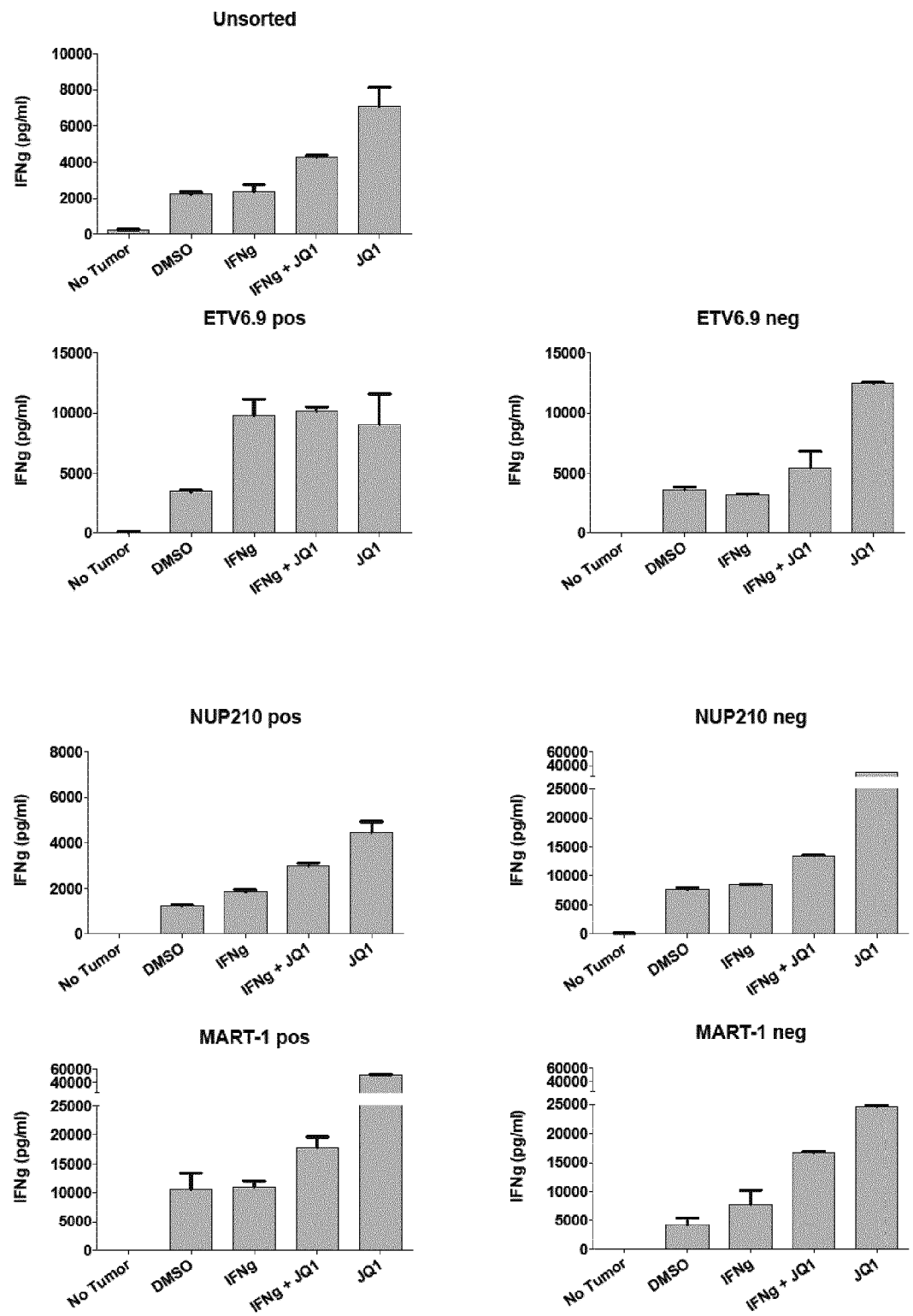
Figure 5:
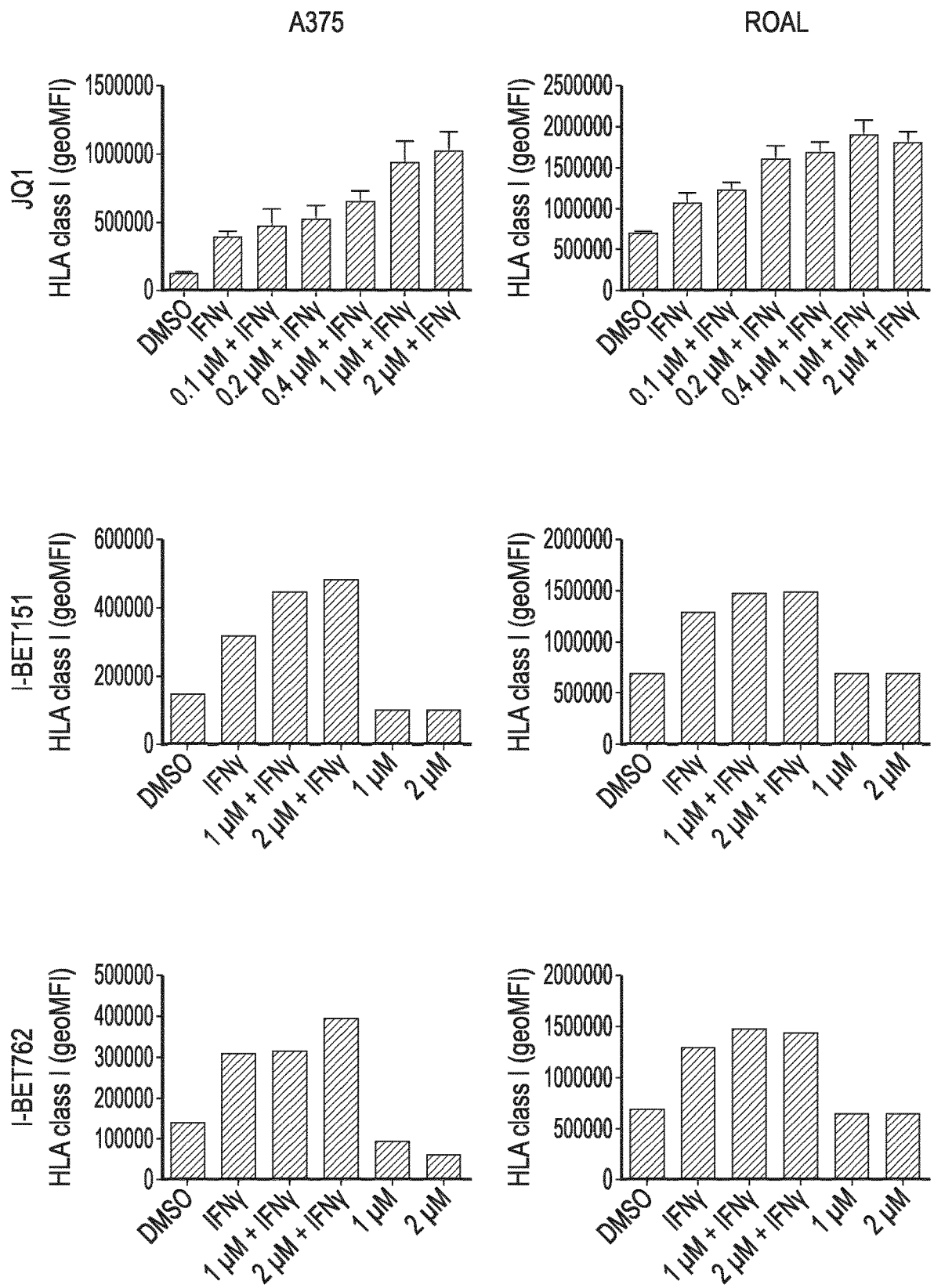
Figure 6:
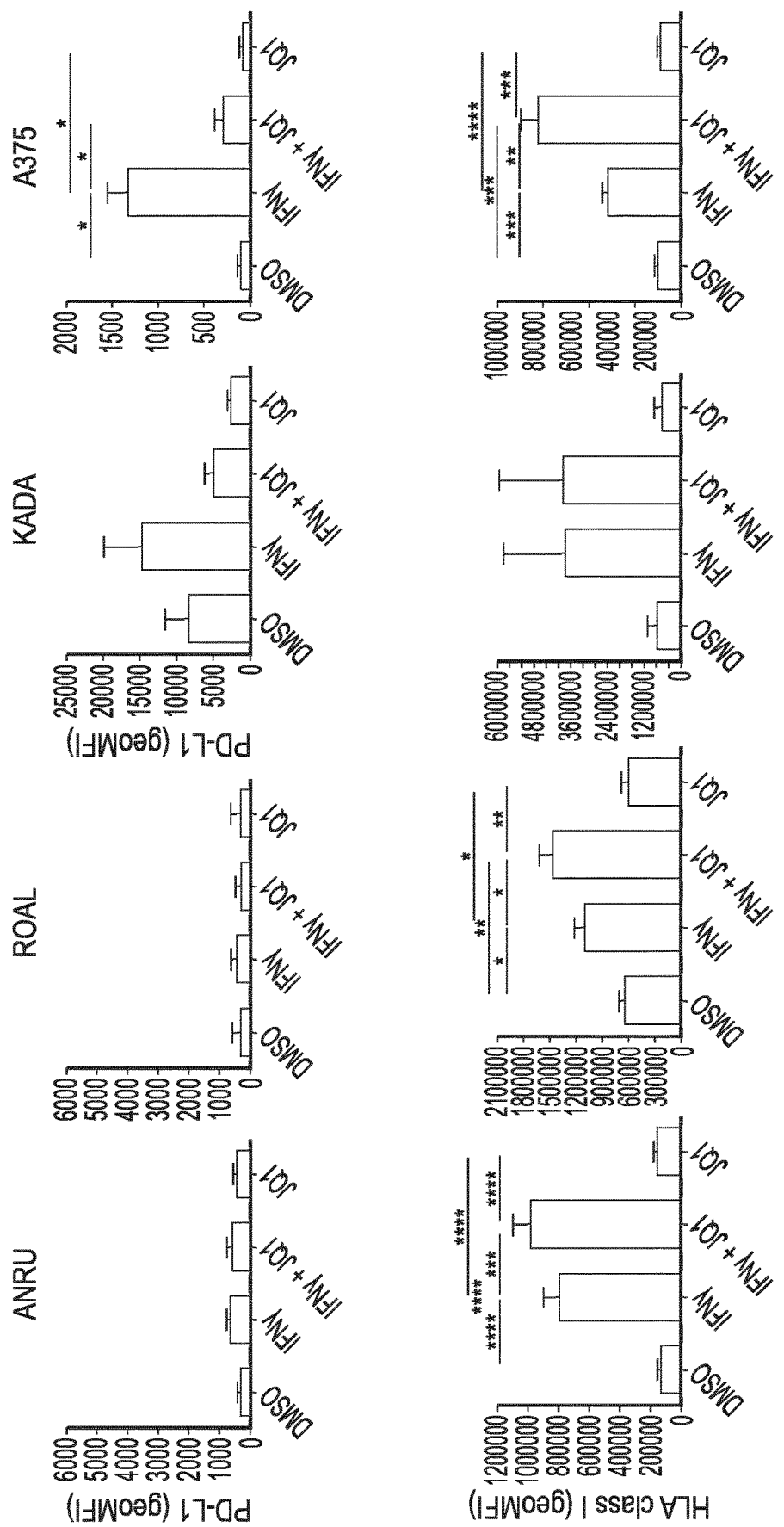
Figure 6:
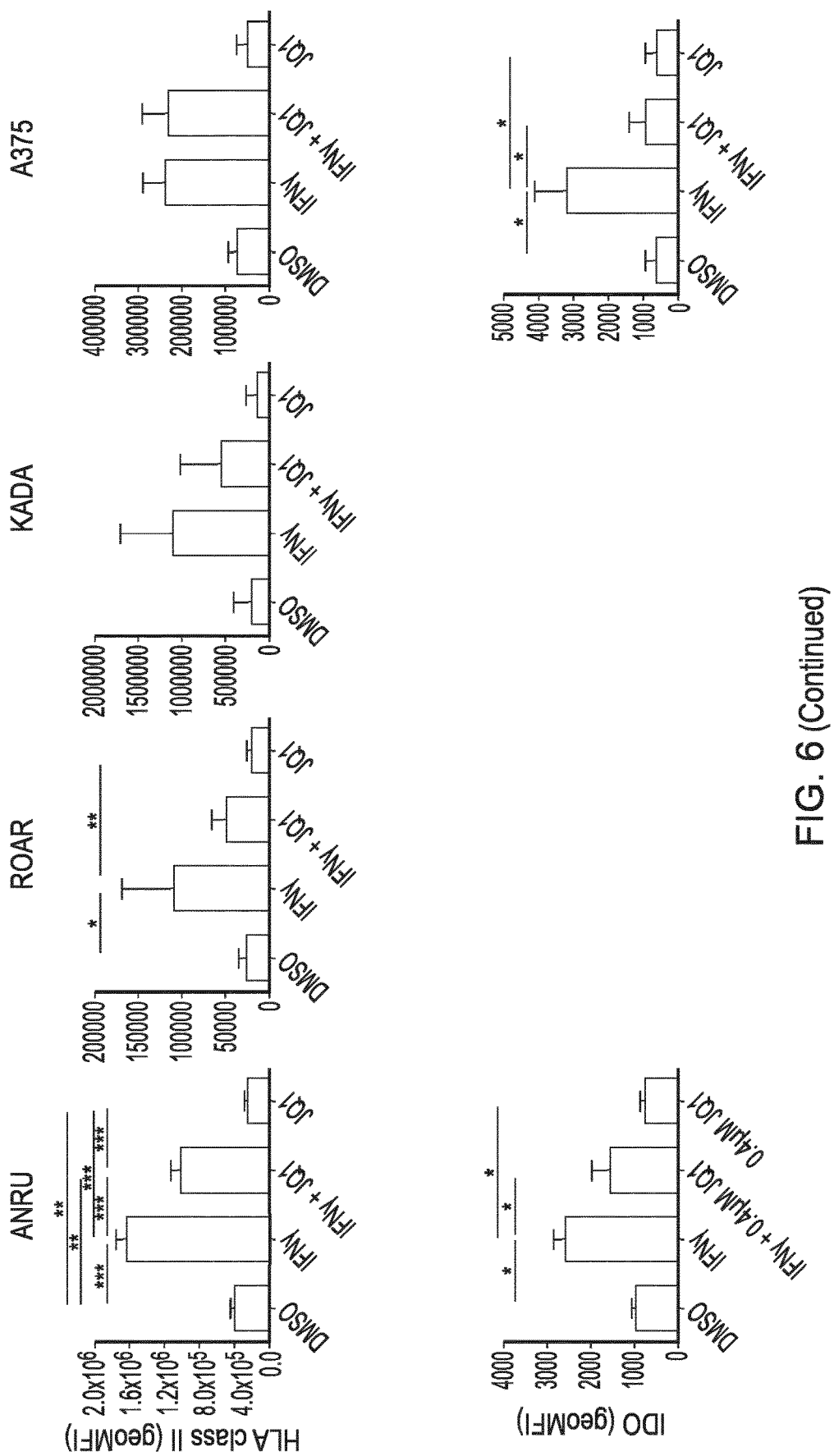
Figure 7:
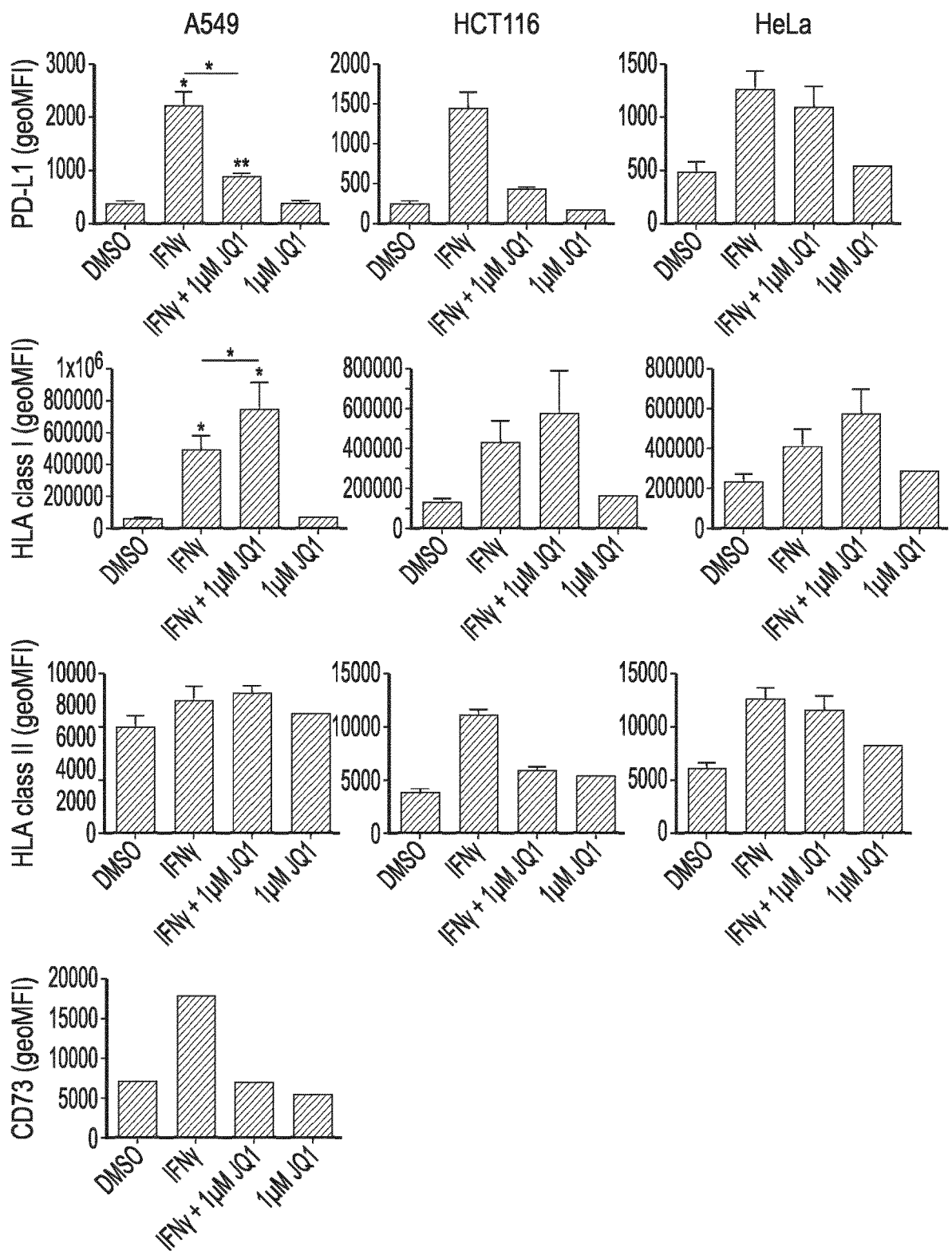
Figure 8A:
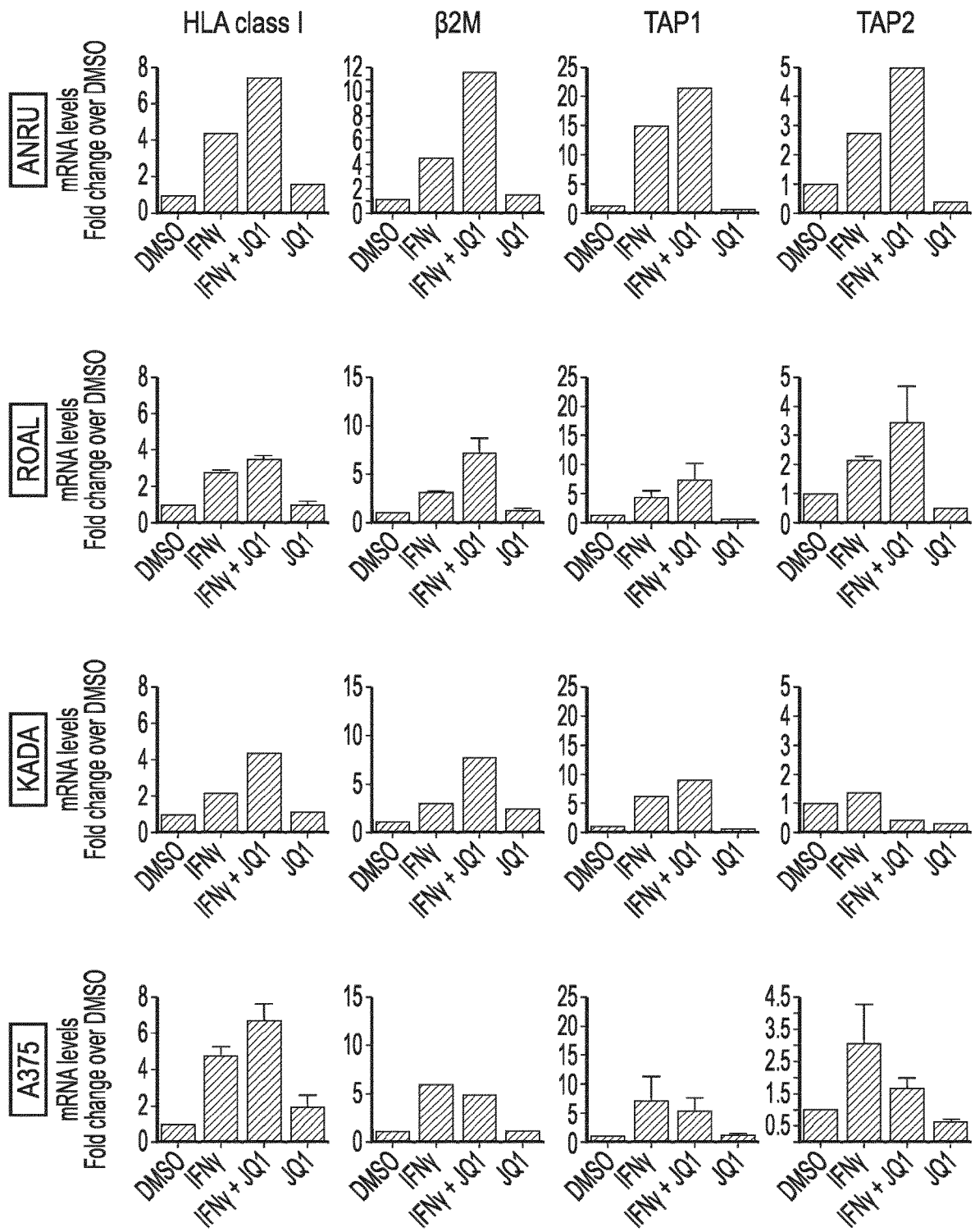
Figure 8A:
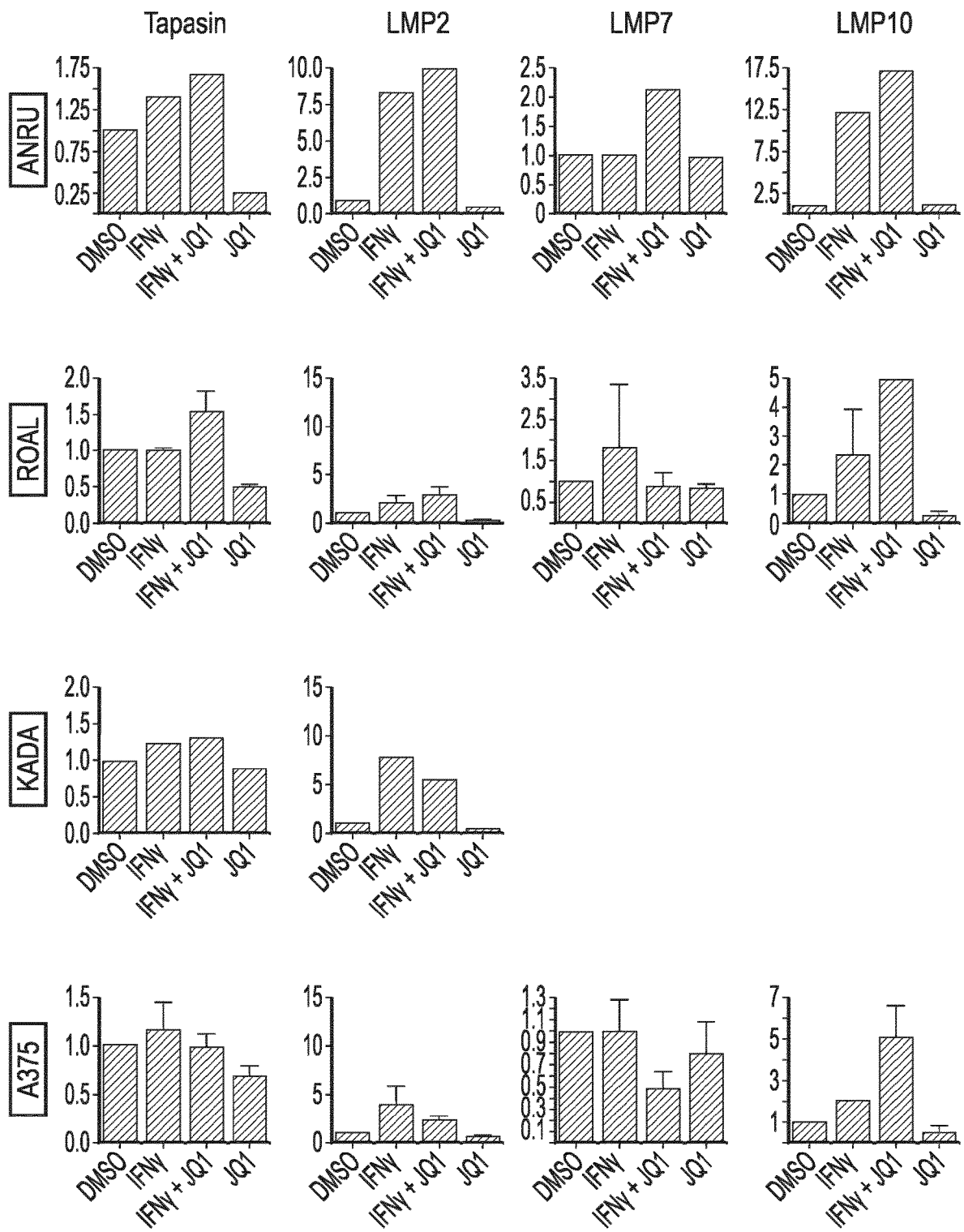
Figure 8B:
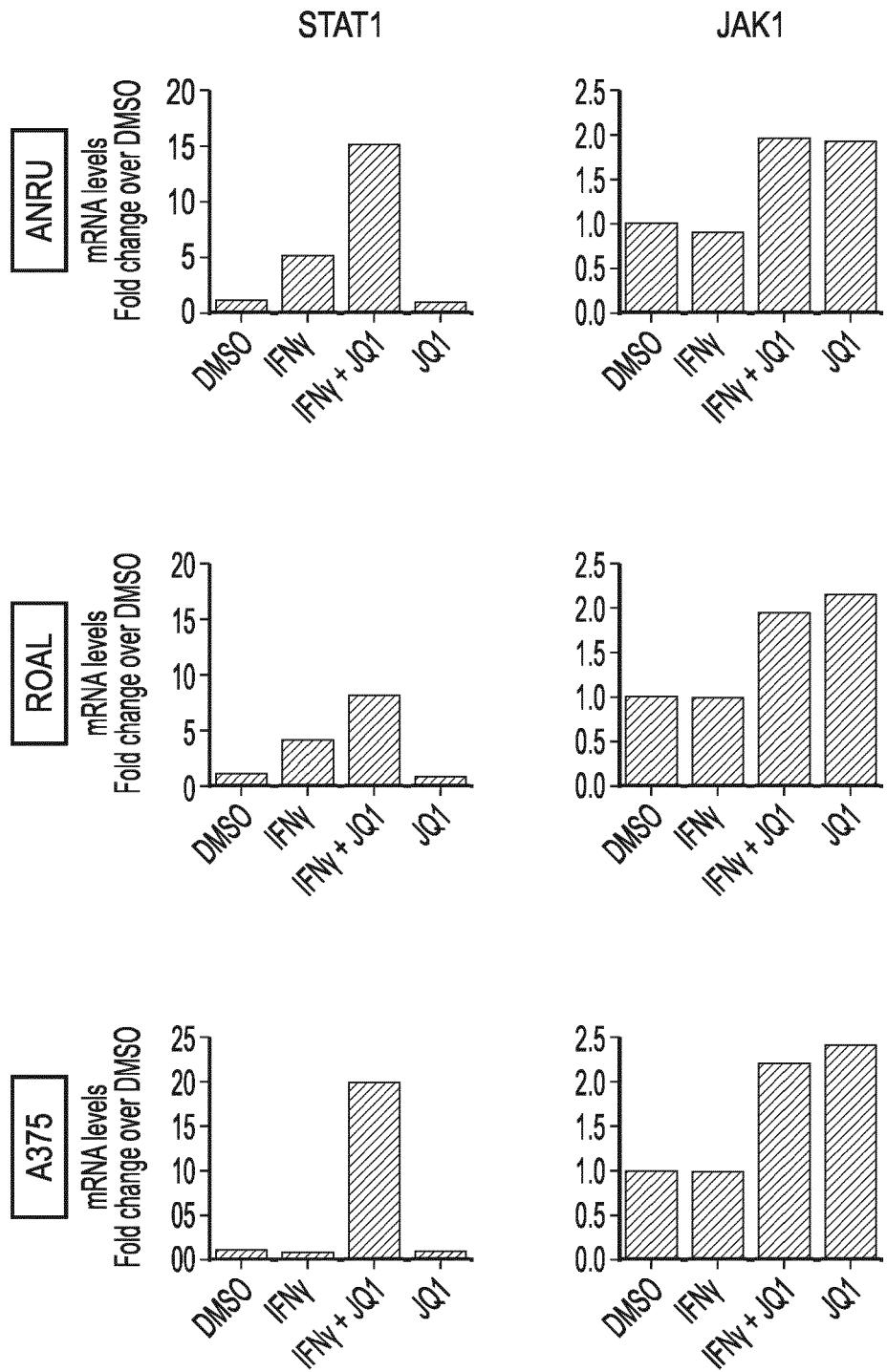
Figure 9:
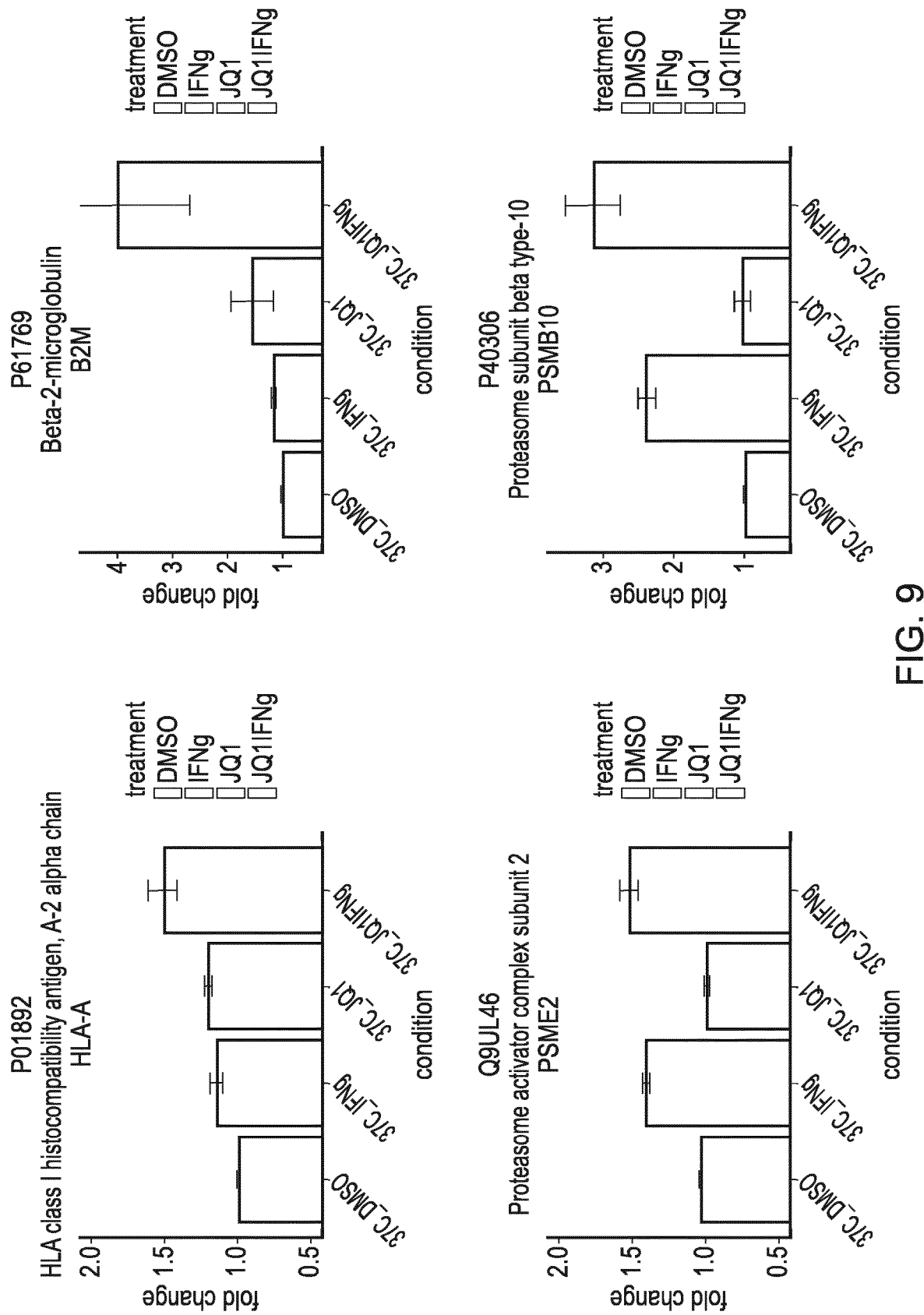
FIG. 9 shows an analysis of protein expression changes by mass spectrometry in lysates of ANRU cells that were incubated for 24 hours with JQ1 and/or IFNγ.
Figure 9:
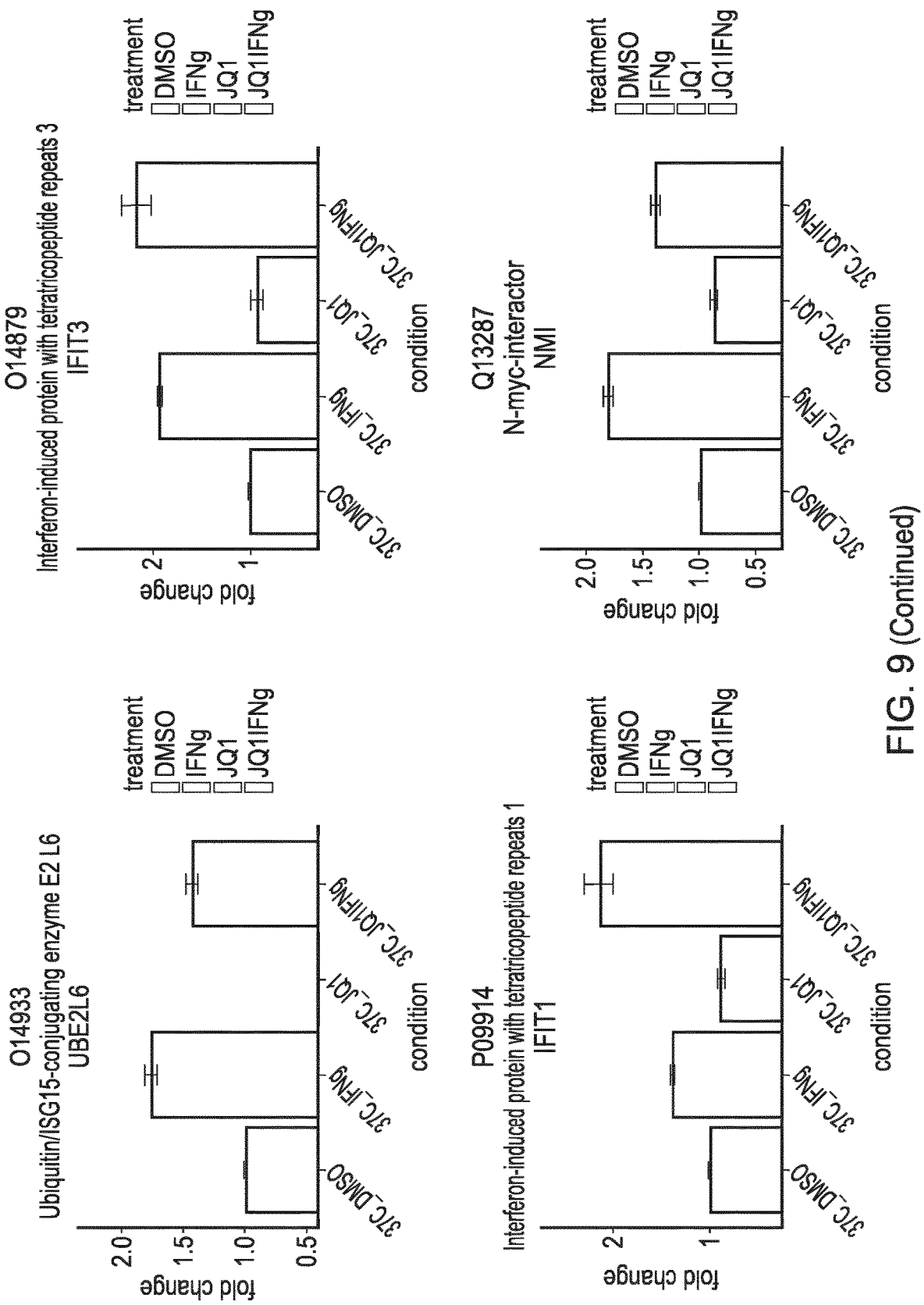
Figure 9:
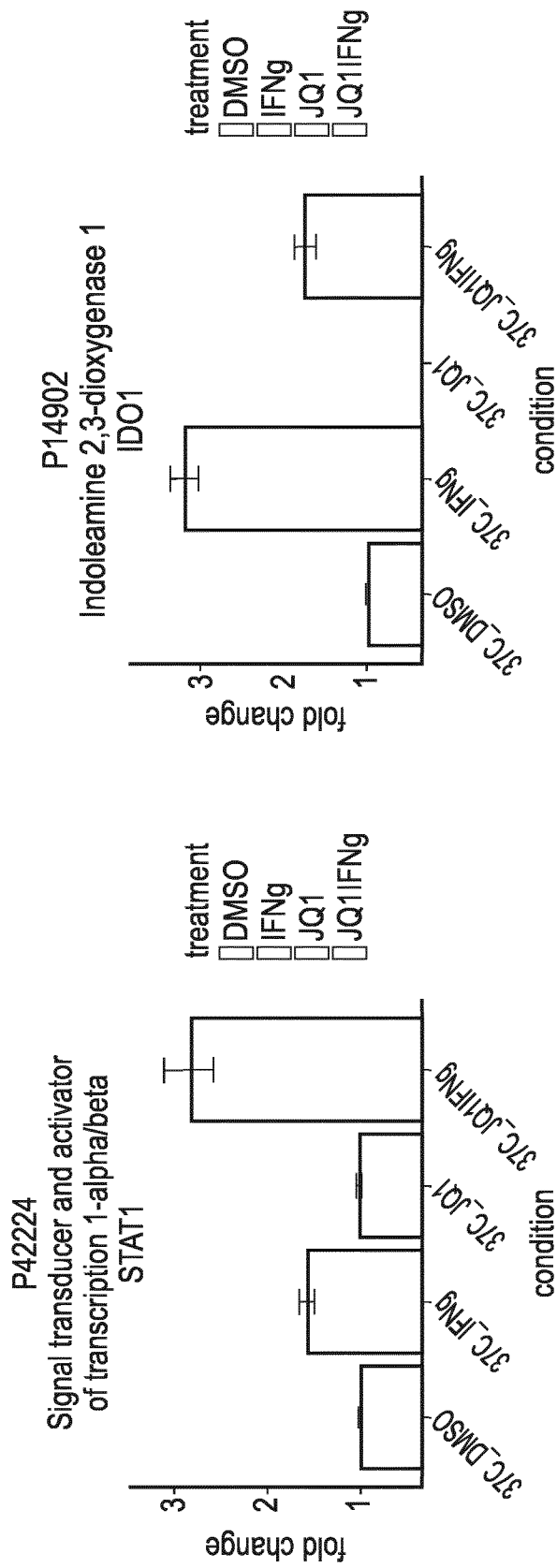
Figure 10A:
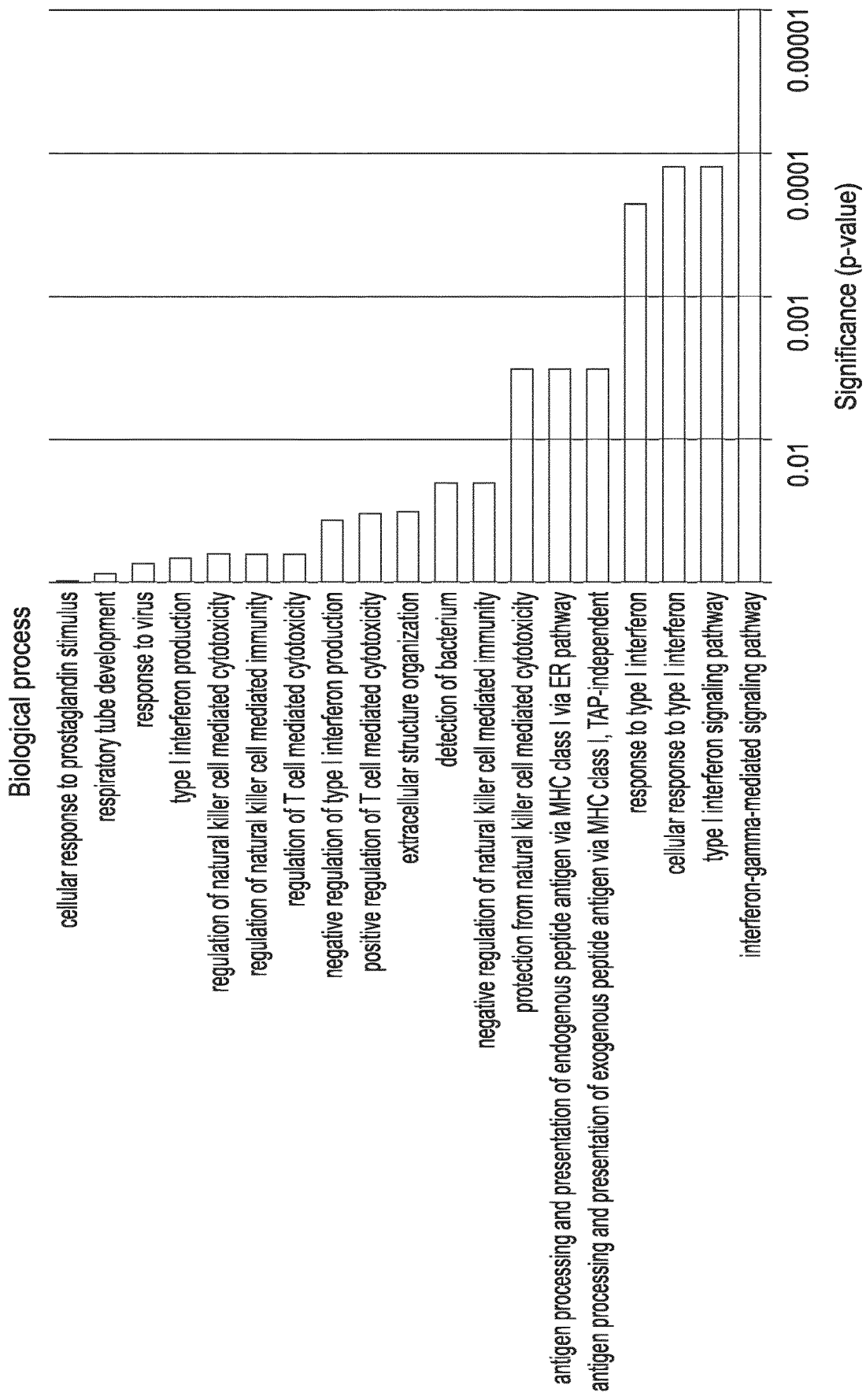
FIG. 10 shows an analysis of protein expression changes by mass spectrometry in lysates of ANRU cells that were incubated for 24 hours with JQ1 and/or IFNγ.
Figure 10B:
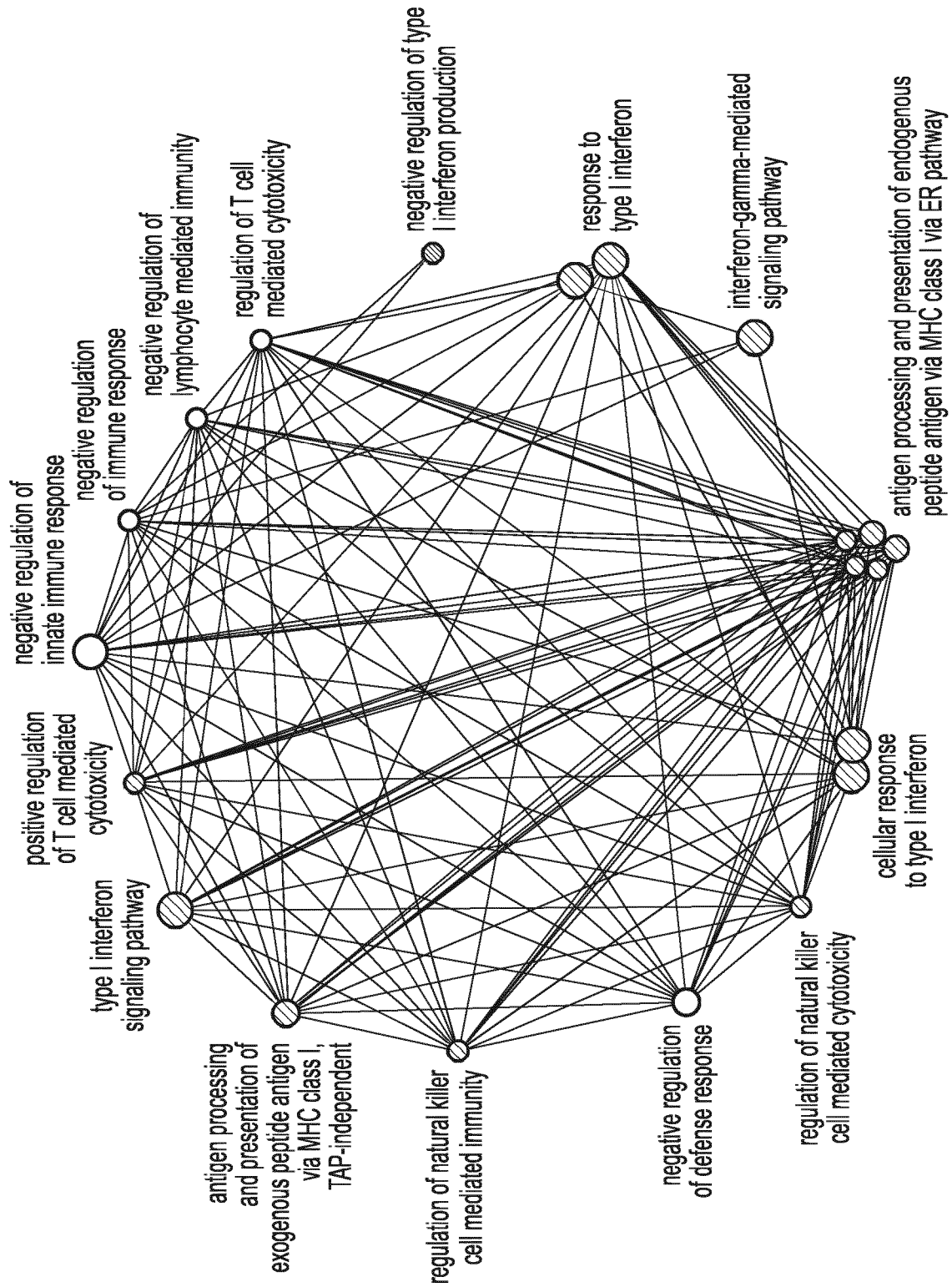
Figure 11:
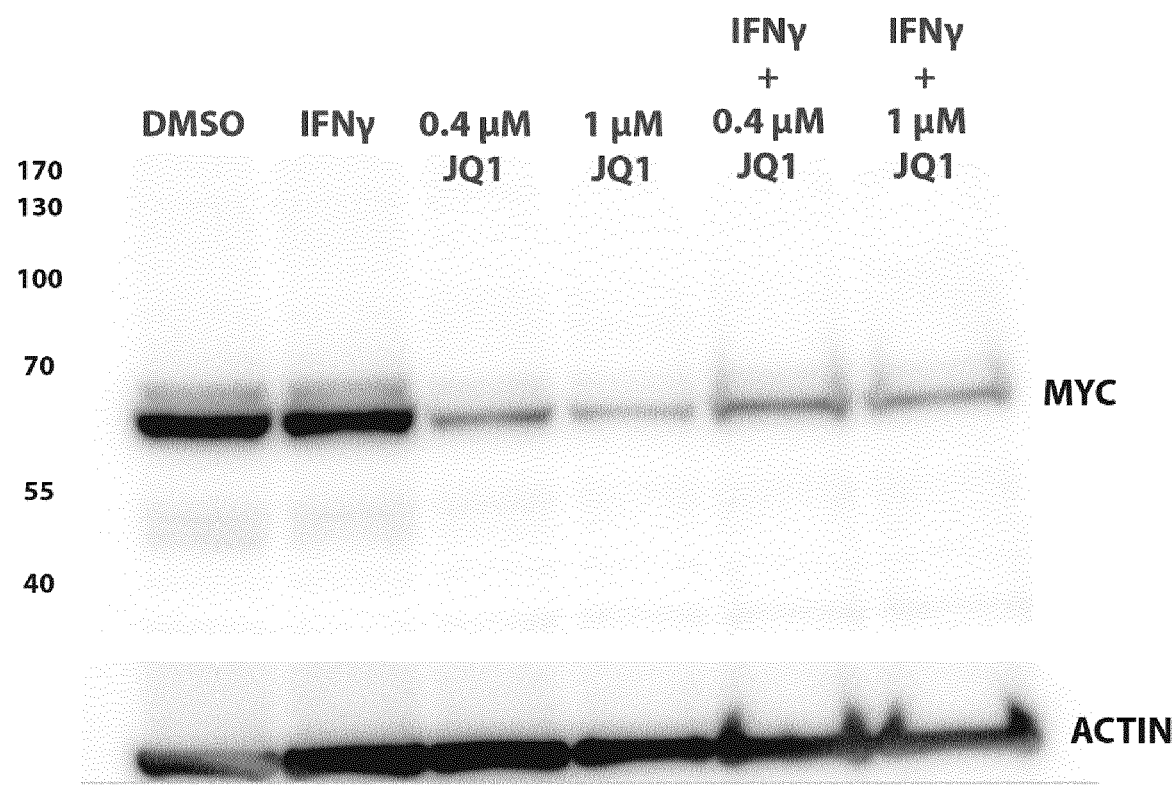
Figure 12:
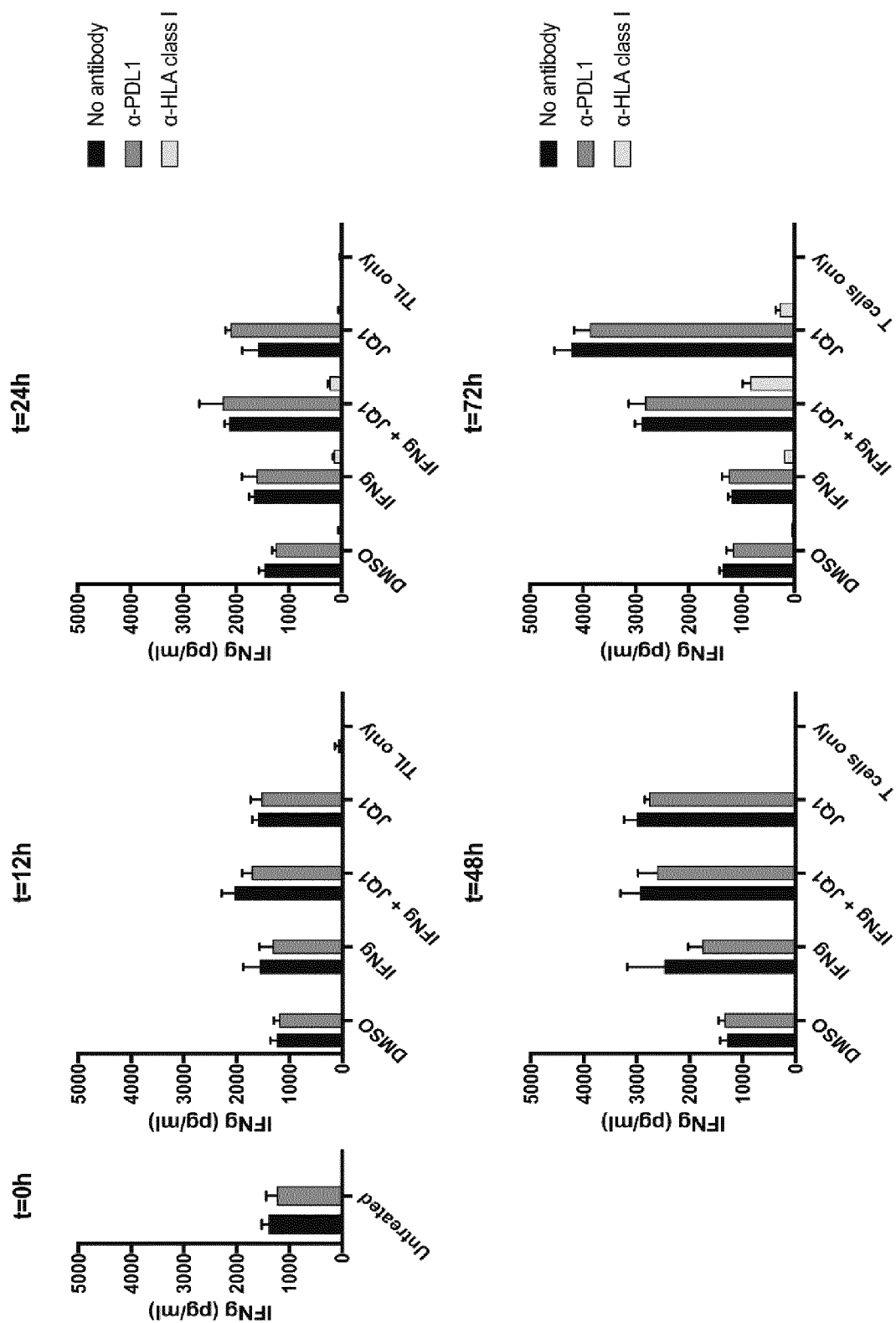

As shown in FIG. 11, MYC expression is downregulated by 72 hours treatment with JQ1 alone or in combination with IFNγ, as indicated by western blot analysis.

REFERENCES

1. Wolchok, J. D. et al. Nivolumab plus Ipilimumab in Advanced Melanoma. N Engl J Med 369, 122-133 (2013).
2. Kenter, G. G. et al. Vaccination against HPV-16 oncoproteins for vulvar intraepithelial neoplasia. N Engl J Med 361, 1838-1847 (2009).
3. Aranda, F. et al. Trial Watch: Adoptive cell transfer for anticancer immunotherapy. Oncoimmunology 3, e28344 (2014).
4. Poschke, I. et al. A phase I clinical trial combining dendritic cell vaccination with adoptive T cell transfer in patients with stage IV melanoma. Cancer Immunol. Immunother. 63, 1061-1071 (2014).
5. Schreibelt, G. et al. Effective Clinical Responses in Metastatic Melanoma Patients after Vaccination with Primary Myeloid Dendritic Cells. Clinical cancer research: an official journal of the American Association for Cancer Research 22, 2155-2166 (2016).
6. Sahin, U. et al. Personalized RNA mutanome vaccines mobilize poly-specific therapeutic immunity against cancer. Nature 72, 1081 (2017).
7. Ott, P. A. et al. An immunogenic personal neoantigen vaccine for patients with melanoma. Nature 348, 69 (2017).
8. Zaretsky, J. M. et al. Mutations Associated with Acquired Resistance to PD-1 Blockade in Melanoma. The New England journal of medicine 375, 819-829 (2016).
9. Zhu, H. et al. BET Bromodomain Inhibition Promotes Anti-tumor Immunity by Suppressing PD-L1 Expression. Cell Reports 16, 2829-2837 (2016).
10. Hogg, S. J. et al. BET-Bromodomain Inhibitors Engage the Host Immune System and Regulate Expression of the Immune Checkpoint Ligand PD-L1. Cell Reports 18, 2162-2174 (2017).
11. Filippakopoulos, P. & Knapp, S. Targeting bromodomains: epigenetic readers of lysine acetylation. Nat Rev Drug Discov 13, 337-356 (2014).
12. Filippakopoulos, P. et al. Selective inhibition of BET bromodomains. Nature 468, 1067-1073 (2010).

13. Zuber, J. et al. RNAi screen identifies Brd4 as a therapeutic target in acute myeloid leukaemia. Nature 478, 524-528 (2011).
14. Puissant, A. et al. Targeting MYCN in neuroblastoma by BET bromodomain inhibition. Cancer Discovery 3, 308-323 (2013).
15. Segura, M. F. et al. BRD4 Sustains Melanoma Proliferation and Represents a New Target for Epigenetic Therapy. Cancer Res. 73, 6264-6276 (2013).
16. Delmore, J. E. et al. BET Bromodomain Inhibition as a Therapeutic Strategy to Target c-Myc. Cell 146, 904-917 (2011).
17. Mertz, J. A. et al. Targeting MYC dependence in cancer by inhibiting BET bromodomains. Proceedings of the National Academy of Sciences of the U.S.A 108, 16669-16674 (2011).
18. Filippakopoulos, P. & Knapp, S. Targeting bromodomains: epigenetic readers of lysine acetylation. Nat Rev Drug Discov 13, 337-356 (2014).
19. Gowrishankar, K. et al. Inducible but Not Constitutive Expression of PD-L1 in Human Melanoma Cells Is Dependent on Activation of NF-κB. PLoS ONE 10, e0123410 (2015).
20. Casey, S. C. et al. MYC regulates the antitumor immune response through CD47 and PD-L1. Science (New York, N.Y.) 352, 227-231 (2016).
21. Selvan, S. R. et al. Establishment of stable cell lines for personalized melanoma cell vaccine. Melanoma Research 20, 280-292 (2010).
22. Spranger, S. et al. Up-Regulation of PD-L1, IDO, and Tregs in the Melanoma Tumor Microenvironment Is Driven by CD8+ T Cells. Science Translational Medicine 5, 200ra116-200ra116 (2013).
23. Patel, S. J. et al. Identification of essential genes for cancer immunotherapy. Nature 17, 10 (2017).
24. Kagoya Y, Nakatsugawa M, Yamashita Y, Ochi T, Guo T, Anczurowski M, Saso K, Butler M O, Arrowsmith C H, Hirano N (2016) BET bromodomain inhibition enhances T cell persistence and function in adoptive immunotherapy models. The Journal of clinical investigation 126:3479-3494. doi: 10.1172/JCI86437
25. Selvan, S. R. et al. Establishment of stable cell lines for personalized melanoma cell vaccine. Melanoma Research 20, 280-292 (2010).
26. Poschke, I. et al. A phase I clinical trial combining dendritic cell vaccination with adoptive T cell transfer in patients with stage IV melanoma. Cancer Immunol. Immunother. 63, 1061-1071 (2014).
Allard, D., Chrobak, P., Allard, B., Messaoudi, N., & Stagg, J. (2018). Targeting the CD73-adenosine axis in immuno-oncology. Immunology Letters. doi.org/10.1016/j.imlet.2018.05.001
Cavallo, F., De Giovanni, C., Nanni, P., Forni, G., & Lollini, P. L. (2011). 2011: the immune hallmarks of cancer. Cancer Immunology, Immunotherapy: CII, 60 (3), 319-326. doi.org/10.1007/s00262-010-0968-0
Dijkstra, K. K., Cattaneo, C. M., Weeber, F., Chalabi, M., van de Haar, J., Fanchi, L. F., et al. (2018). Generation of Tumor-Reactive T Cells by Co-culture of Peripheral Blood Lymphocytes and Tumor Organoids. Cell. doi.org/10.1016/j.cell.2018.07.009
Donia, M., Andersen, R., Kjeldsen, J. W., Fagone, P., Munir, S., Nicoletti, F., et al. (2015). Aberrant Expression of MHC Class II in Melanoma Attracts Inflammatory Tumor-Specific CD4+T-Cells, Which Dampen CD8+T-cell Antitumor Reactivity. Cancer Research, 75 (18), 3747-3759. doi.org/10.1158/0008-5472.CAN-14-2956
Fransen, M. F., Sluijter, M., Morreau, H., Arens, R., & Melief, C. J. M. (2011). Local Activation of CD8 T Cells and Systemic Tumor Eradication without Toxicity via Slow Release and Local Delivery of Agonistic CD40 Antibody. Clinical Cancer Research: an Official Journal of the American Association for Cancer Research, 17 (8), 2270-2280. doi.org/10.1158/1078-0432.CCR-10-2888
Fransen, M. F., van der Sluis, T. C., Ossendorp, F., Arens, R., & Melief, C. J. M. (2013). Controlled Local Delivery of CTLA-4 Blocking Antibody Induces CD8+T-Cell-Dependent Tumor Eradication and Decreases Risk of Toxic Side Effects. Clinical Cancer Research: an Official Journal of the American Association for Cancer Research, 19 (19), 5381-5389. doi.org/10.1158/1078-0432.CCR-12-0781
Hemon, P., Jean-Louis, F., Ramgolam, K., Brignone, C., Viguier, M., Bachelez, H., et al. (2011). MHC Class II Engagement by Its Ligand LAG-3 (CD223) Contributes to Melanoma Resistance to Apoptosis. Journal of Immunology (Baltimore, Md.: 1950), 186 (9), 5173-5183. doi.org/10.4049/jimmunol.1002050
Holmgaard, R. B., Zamarin, D., Li, Y., Gasmi, B., Munn, D. H., Allison, J. P., et al. (2015). Tumor-Expressed IDO Recruits and Activates MDSCs in a Treg-Dependent Manner. Cell Reports, 13(2), 412-424. doi.org/10.1016/j.celrep.2015.08.077
Hornyák, L., Dobos, N., Koncz, G., Karányi, Z., Páll, D., Szabó, Z., et al. (2018). The Role of Indoleamine-2,3-Dioxygenase in Cancer Development, Diagnostics, and Therapy. Frontiers in Immunology, 9, 5427. doi.org/10.3389/fimmu.2018.00151
Ishihara, J., Fukunaga, K., Ishihara, A., Larsson, H. M., Potin, L., Hosseinchi, P., et al. (2017). Matrix-binding checkpoint immunotherapies enhance antitumor efficacy and reduce adverse events. Science Translational Medicine, 9 (415), eaan0401. doi.org/10.1126/scitranslmed.aan0401
Khan, A. N. H., Gregorie, C. J., & Tomasi, T. B. (2008). Histone deacetylase inhibitors induce TAP, LMP, Tapasin genes and MHC class I antigen presentation by melanoma cells. Cancer Immunology, Immunotherapy: CII, 57 (5), 647-654. doi.org/10.1007/s00262-007-0402-4
Kim, Y. H., Gratzinger, D., Harrison, C., Brody, J. D., Czerwinski, D. K., Ai, W. Z., et al. (2012). In situ vaccination against mycosis fungoides by intratumoral injection of a TLR9 agonist combined with radiation: a phase 1/2 study. Blood, 119 (2), 355-363. doi.org/10.1182/blood-2011-05-355222
Landsberg, J., Kohlmeyer, J., Renn, M., Bald, T., Rogava, M., Cron, M., et al. (2012). Melanomas resist T-cell therapy through inflammation-induced reversible dedifferentiation. Nature, 490 (7420), 412-416. doi.org/10.1038/nature11538
Marabelle, A., Tselikas, L., de Baere, T., & Houot, R. (2017). Intratumoral immunotherapy: using the tumor as the remedy. Annals of Oncology, 28 (suppl 12), xii33-xii43. doi.org/10.1093/annonc/mdx683
McGranahan, N., Rosenthal, R., Hiley, C. T., Rowan, A. J., Watkins, T. B. K., Wilson, G. A., et al. (2017). Allele-Specific HLA Loss and Immune Escape in Lung Cancer Evolution. Cell, 171 (6), 1259-1271.e11. doi.org/10.1016/j.cell.2017.10.001
Munn, D. H., & Mellor, A. L. (2013). Indoleamine 2, 3 dioxygenase and metabolic control of immune responses. Trends in Immunology, 34 (3), 137-143. doi.org/10.1016/j.it.2012.10.001
Respa, A., Bukur, J., Ferrone, S., Pawelec, G., Zhao, Y., Wang, E., et al. (2011). Association of IFN-gamma signal transduction defects with impaired HLA class I antigen processing in melanoma cell lines. *Clinical Cancer Research: an Official Journal of the American Association for Cancer Research,* 17 (9), 2668-2678. doi.org/10.1158/1078-0432.CCR-10-2114

Sagiv-Barfi, I., Czerwinski, D. K., Levy, S., Alam, I. S., Mayer, A. T., Gambhir, S. S., & Levy, R. (2018). Eradication of spontaneous malignancy by local immunotherapy. *Science Translational Medicine,* 10 (426), eaan4488. doi.org/10.1126/scitranslmed.aan4488

Setiadi, A. F., Omilusik, K., David, M. D., Seipp, R. P., Hartikainen, J., Gopaul, R., et al. (2008). Epigenetic Enhancement of Antigen Processing and Presentation Promotes Immune Recognition of Tumors. *Cancer Research,* 68 (23), 9601-9607. doi.org/10.1158/0008-5472.CAN-07-5270 van der Burg, S. H., Arens, R., Ossendorp, F., van Hall, T., & Melief, C. J. M. (2016). Vaccines for established cancer: overcoming the challenges posed by immune evasion. Nature Reviews. Cancer, 16 (4), 219-233. doi.org/10.1038/nrc.2016.16

Woo, S.-R., Turnis, M. E., Goldberg, M. V., Bankoti, J., Selby, M., Nirschl, C. J., et al. (2012). Immune inhibitory molecules LAG-3 and PD-1 synergistically regulate T-cell function to promote tumoral immune escape. *Cancer Research,* 72(4), 917-927. doi.org/10.1158/0008-5472.CAN-11-1620

Zaretsky, J. M., Garcia-Diaz, A., Shin, D. S., Escuin-Ordinas, H., Hugo, W., Hu-Lieskovan, S., et al. (2016). Mutations Associated with Acquired Resistance to PD-1 Blockade in Melanoma. *The New England Journal of Medicine,* 375 (9), 819-829. doi.org/10.1056/NEJMoa1604958

The invention claimed is:

1. A method for the treatment of cancer in a subject, the method comprising the step of administering to the subject a composition comprising tumor cells, wherein said tumor cells are tumor cells derived from the subject and contacted ex vivo with an inhibitor of a bromodomain and extra-terminal domain family member (BET inhibitor), wherein the composition is treated such that the cells contained in the composition cannot proliferate when administered to the subject in vivo, and wherein said treatment of said composition comprises subjecting the cells to ionizing radiation.

2. The method for the treatment of cancer according to claim 1, wherein the treatment is combined with the systemic or localized administration of a drug selected from the group consisting of immunomodulatory compound, angiogenesis inhibitors, chemotherapeutics, and c-Myc inhibitors.

3. The method according to claim 1, wherein said tumor cells are primary tumor cells.

4. The method according to claim 1, wherein the cancer is a melanoma, lung cancer, colorectal cancer or cervical cancer.

5. The method according to claim 1, wherein the BET inhibitor is selected from the group consisting of: JQ1, iBET-151 and iBET-762.

* * * * *